United States Patent [19]
Briggs et al.

[11] Patent Number: 5,498,696
[45] Date of Patent: Mar. 12, 1996

[54] STEROL REGULATORY ELEMENT BINDING PROTEINS AND THEIR USE IN SCREENING ASSAYS

[75] Inventors: Michael R. Briggs, Carrollton; Michael S. Brown, Dallas; Joseph L. Goldstein, Dallas; Xiaodong Wang, Dallas, all of Tex.

[73] Assignee: Board of Regents, The University of Texas System, Austin, Tex.

[21] Appl. No.: 61,697

[22] Filed: May 13, 1993

[51] Int. Cl.$^6$ .................................................. C07K 14/47
[52] U.S. Cl. ..................................................... 530/350
[58] Field of Search ............................ 435/70.3, 172.3, 435/240.2; 530/350; 536/24.1

[56] References Cited

U.S. PATENT DOCUMENTS

| | | | |
|---|---|---|---|
| 4,935,363 | 6/1990 | Brown et al. | 435/172.3 |
| 5,215,910 | 6/1993 | Brown et al. | 435/240.2 |
| 5,256,545 | 10/1993 | Brown et al. | 435/69.1 |

FOREIGN PATENT DOCUMENTS

WO88/07579  10/1988  WIPO.

OTHER PUBLICATIONS

Agnant et al., (1989) Biochem. J. 263, 753–760.
Osborne et al. (1992) J. Biol. Chem. 267(26) 18973–18982.
Briggs et al., (1986) Science 234, 47–52.
Brown et al., (1986) Science 232, 34–47.
Smith et al., (1990) J. Biolog. Chem. 265(4), 2306–2310.
Briggs et al., "Nuclear Protein that Binds Sterol Regulatory Element of Low Density Lipoprotein Receptor Promotor," *J. Biol. Chem.*, 268(19):14490–14496, 1993.
Hua et al., "SREBP–2, a Second Basic–Helix–Loop–Helix–Leucine Zipper Protein that Stimulates Transcription by Binding to a Sterol Regulatory Element," *Proc. Natl. Acad. Sci. USA* 90:11603–11607, 1993.
Osborne, "Single Nucleotide Resolution of Sterol Regulatory Region in Promoter for 3–Hydroxy–3–Methylglutaryl Coenzylme A Reductease," *J. Biol. Chem.*, 266(21):13947–13951, 1991.
Wang et al., "Nuclear Protein That Binds Sterol Regulatory Element of Low Density Lipoprotein Receptor Promoter," *J. Biol. Chem.*, 268(19):14497–14504, 1993.
Yokoyama et al., "SREBP–1, a Basic–Helix–Loop–Helix–Leucine Zipper Protein That Controls Transcription of the Low Density Lipoprotein Receptor Gene," *Cell*, 75:187–197, 1993.
Ayer et al., "Mad: A Heterodimeric Partner for Max That Antagonizes Myc Transcriptional Activity," *Cell*, 72:211–222, 1993.
Gil et al., "Purification of A Protein Doublet That Binds to Six TGG–Containing Sequences in the Promoter for Hamster 3–Hydroxy–3–Methylglutaryl–Coenzyme A Reductase," *J. Biol. Chem.*, 263(35):19009–19019, 1988.
Gil et al., "Multiple Genes Encode Nuclear Factor 1–Like Proteins That Bind to the Promoter for 3–Hydroxy–3–Methylglutaryl–Coenzyme A Reductase," *Proc. Natl. Acad. Sci. USA*, 85:8963–8967, 1988.
Rajavashisth et al., "Identification of a Zinc Finger Protein That Binds to the Sterol Regulatory Element," *Science*, 245:640–643, 1989.
Stark et al., "Common Double–and Single–Stranded DNA Binding actor for a Sterol Regulatory Element," *Proc. Natl. Acad. Sci. USA*, 89:2180–2184 1992.

*Primary Examiner*—Mindy Fleisher
*Assistant Examiner*—Terry A. McKelvey
*Attorney, Agent, or Firm*—Arnold, White & Durkee

[57] ABSTRACT

A nuclear protein which binds sterol regulatory elements (SREs), such as SRE-1 of the low density lipoprotein (LDL) receptor gene, and mediates sterol-regulated transcription of the LDL receptor gene is disclosed. Also described are screening assay and methods for the identification of agents capable of promoting LDL receptor gene transcription for use in reducing plasma cholesterol and treating the various medical problems associated therewith.

4 Claims, 16 Drawing Sheets

|2|   5' AAAATCACCCCACTGC 3'

|3|   5' AAACTCCTCCCCCTGC 3'

|2|3|   5' AAAATCACCCCACTGCAAACTCCTCCCCCTGC 3'

|2*3|   5' AAAAgaACCCtaTGCAAACTCCTCCCCCTGC 3'

FIGURE 1A

5' TGAAGCTTGCATGCCTGCAGGTCGA↓CTCGACTCTAGAGGG

TATATAATGGATCCCCGGGTACCGAGCTCGAATTCATCAGCTTGG

CGAGATTTTCAGGAGCTAAHHAHCTAAAATG 3'

FIGURE 1B

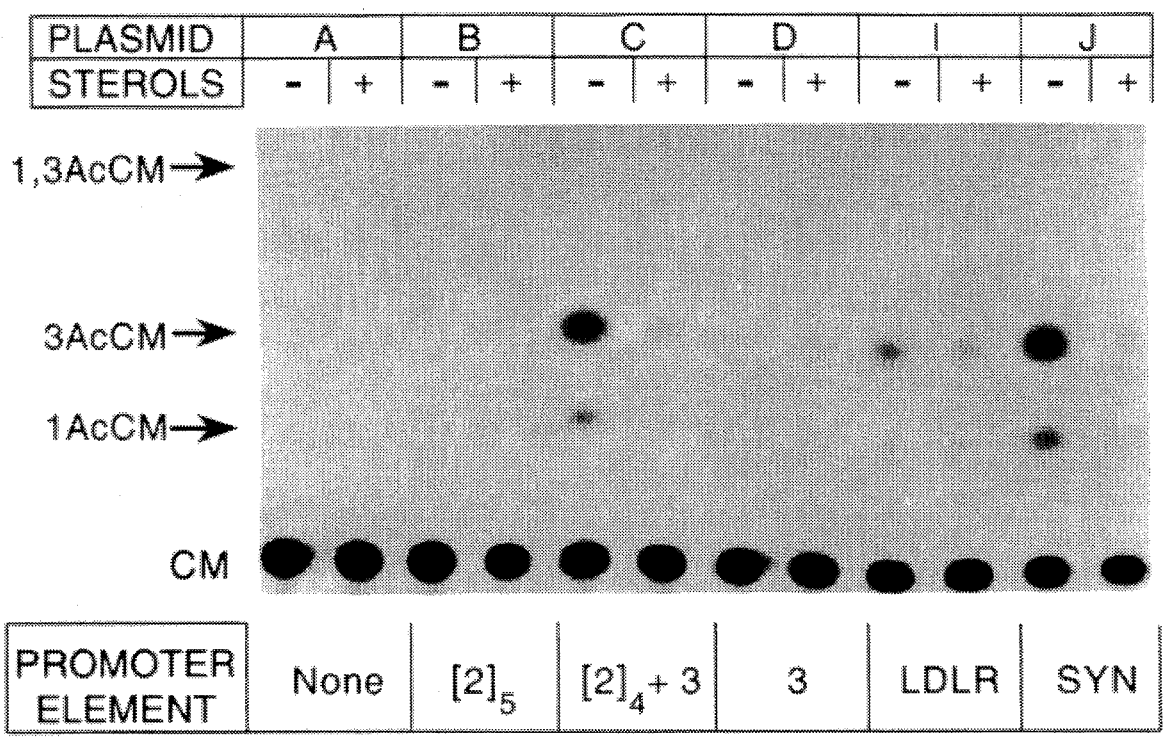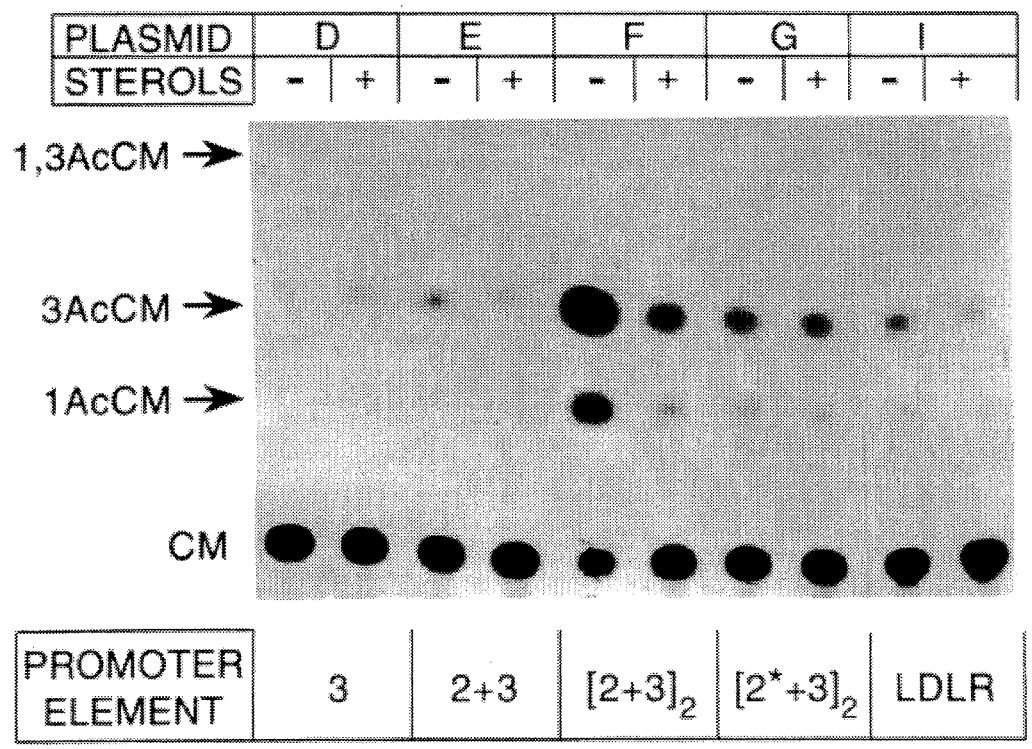
FIG.2

FIG.6A
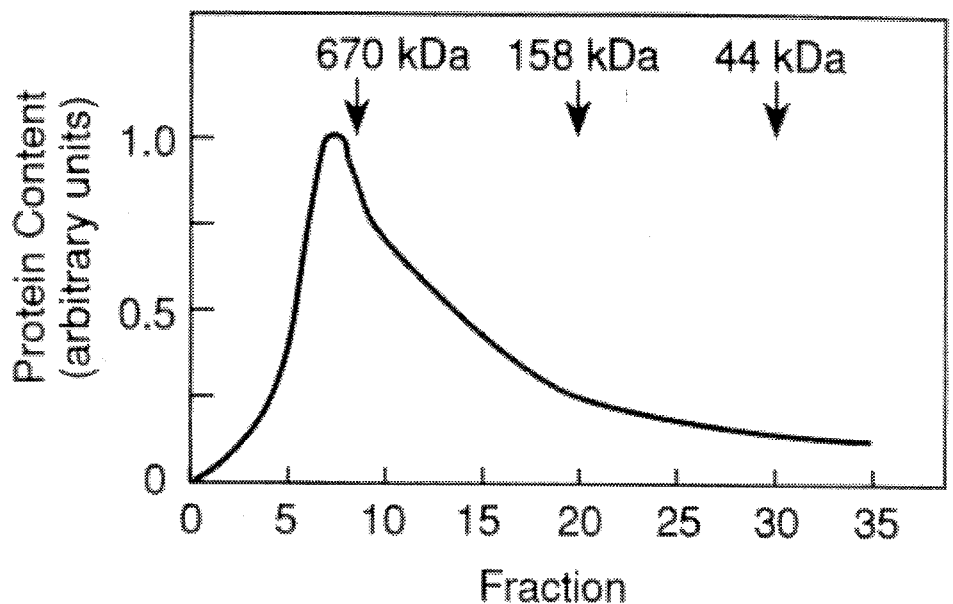
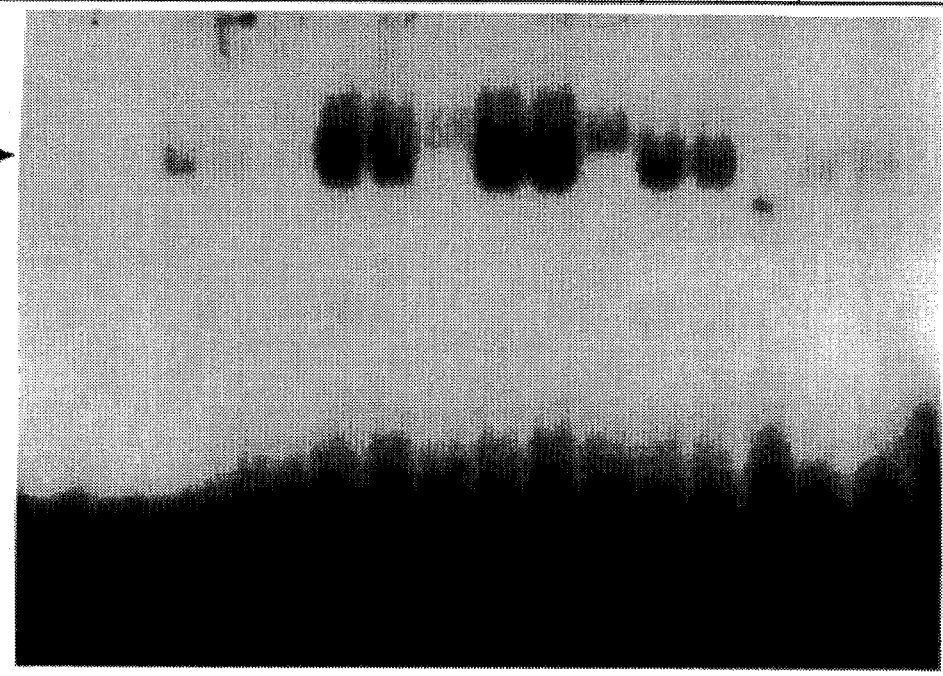
FIG.6B

STEROL REGULATORY ELEMENT BINDING PROTEINS AND THEIR USE IN SCREENING ASSAYS

The government owns rights in the present invention pursuant to Grants HL 20948 and 5F32HL07833 from the National Institutes of Health.

BACKGROUND OF THE INVENTION

1. Field of the Invention

The present invention relates generally to proteins which regulate genes and to methods for altering gene expression, cellular function and metabolism. In particular, the invention concerns nuclear proteins which bind sterol regulatory elements (SREs), such as the SRE-1 (SEQ ID NO:27, for example) of the low density lipoprotein (LDL) receptor gene, and methods for identifying candidate substances which stimulate SRE-1-mediated gene transcription. Such substances are contemplated for use in reducing plasma cholesterol levels and, thereby, for controlling hypercholesterolemia and its associated diseases.

2. Description of the Related Art

There is currently relatively little knowledge concerning feedback suppression mechanisms involved in eukaryotic gene regulation. In animal cells, most attention has focused on positively-regulated systems in which hormones, metabolic inducers, and developmental factors increase transcription of genes. These inducing agents are generally thought to activate or form complexes with proteins that stimulate transcription by binding to short sequences of 10 to 20 base pairs (bp) in the 5'-flanking region of the target gene. Such elements, termed GRE, MRE, and IRE have been reported for glucocorticoid, metal and interferon regulatory elements, respectively (Yamamoto, 1985; Stuart et al., 1984; Goodbourn et al., 1986).

Important advances have been made recently concerning other DNA segments which are capable of conferring control capability to known genes in eukaryotic systems. For example, transcription of the gene for the low density lipoprotein (LDL) receptor is regulated by a 10 base pair (bp) element in the 5' flanking region designated sterol regulatory element-1 (SRE-1, SEQ ID NO:27) (Goldstein and Brown, 1990; U.S. Pat. No. 4,935,363). The receptor provides cholesterol to cells by binding and internalizing LDL, a plasma cholesterol transport protein. When cellular cholesterol demands are high, as when cells are grown in the absence of sterols, this element is transcriptionally active, the cells produce large numbers of LDL receptors and LDL is internalized rapidly. On the other hand, when sterols accumulate within cells, the SRE-1 is silenced, and cells reduce the number of LDL receptors, thereby preventing cholesterol over accumulation. This feedback regulatory system controls not only the cholesterol content of cells, but also that of plasma (Brown and Goldstein, 1986). When hepatic LDL receptors are repressed by intracellular accumulation of dietary cholesterol, LDL is not taken up into the liver at a normal rate, and the lipoprotein builds up to high levels in the blood.

The 10 bp SRE-1 (SEQ ID NO:27) lies within a 16-base pair (bp) sequence, designated Repeat 2 (SEQ ID NO:22), that is 53 bp upstream of the transcription start site of the LDL receptor gene (Smith et al., 1990). This sequence is the central member of a series of three imperfect repeats in the 5' flanking region, (Repeats 1; 2, SEQ ID NO:22; and 3, SEQ ID NO:23), all of which are required for high level transcription (Goldstein and Brown, 1990; Smith et al., 1990; Südhof et al., 1987). Repeats 1 and 3 (SEQ ID NO:23) bind Sp1, a constitutive transcription factor. Mutations in any of the three repeat sequences abolish high-level transcription in sterol-deprived cells (Smith et al., 1990; Südhof et al., 1987; Dawson et al., 1988).

The activity of Repeats 1 and 3 (SEQ ID NO:23), although necessary, is not sufficient for high level transcription. An additional positive contribution is required from Repeat 2 (SEQ ID NO:22), which does not bind Sp1 (Smith et al., 1990; Südhof et al., 1987; Dawson et al., 1988). Mutational analysis suggests that Repeat 2 (SEQ ID NO:22) binds a conditionally positive transcription factor that is active only under conditions of sterol deprivation (Smith et al., 1990). When sterols are added to cells, the contribution of Repeat 2 (SEQ ID NO:22) is abolished, and the rate of transcription falls.

The nucleotides within Repeat 2 (SEQ ID NO:22) that are necessary for its transcriptional activity have been delineated partially through in vitro mutagenesis and expression studies in permanently transfected CHO cells. The relevant nucleotides include the SRE-1 10 bp stretch which has the sequence ATCACCCCAC (SEQ ID NO:27) (Smith et al., 1990). The essential elements of this sequence have been shown to be conserved in evolution as far back as the last common ancestor of humans and frogs (Mehta et al., 1991).

Unfortunately, despite the elucidation of the SRE-1 DNA sequence (SEQ ID NO:27), the nature of the putative transcription factor that binds to SRE-1 remained unknown. Two candidates have been proposed (Rajavashisth et al., 1989; Stark et al., 1992), but the proteins in these reports did not show specific binding which precisely correlated with the transcriptional activity of modified SRE-1 elements, and purification of the putative binding proteins was not reported.

The identification of a protein which binds to the SRE-1 sequence and functions to promote transcription would be particularly advantageous. Not only would such a transcription factor be useful in terms of furthering an understanding of eukaryotic gene control in general, but it would also provide a powerful tool for directly and indirectly regulating specific gene expression. A purified SRE-1 binding protein would be extremely useful as the central component in screening assays to identify pharmacological agents capable of altering gene transcription, and particularly, substances capable of promoting LDL receptor gene transcription, especially those which do so even in the presence of sterols which normally down regulate the receptor. Such compounds would act as agents to reduce plasma LDL-cholesterol levels and would represent a significant medical breakthrough.

SUMMARY OF THE INVENTION

The present invention seeks to overcome these and other drawbacks inherent in the prior art by providing a purified DNA binding protein which binds to the sterol regulatory element SRE-1 (SEQ ID NO:27) and functions to promote SRE-1-mediated gene transcription, such as low density lipoprotein (LDL) receptor gene transcription. Also disclosed are advantageous methods for identifying candidate substances which stimulate SRE-1-mediated gene transcription and LDL receptor production. The invention is ultimately directed to identifying new cholesterol-lowering agents capable of stimulating LDL receptor expression, which may even act in the presence of sterols, for use in controlling hypercholesterolemia and the various disease states associated with this condition.

The DNA binding protein of the present invention has been termed the sterol regulatory element (SRE-1) binding protein, or SREBP. In the present text, the terms "SREBP", SRE-1 binding protein and DNA binding protein are used interchangeably and each refer to a proteinaceous composition which is isolatable from mammalian cell nuclei and which is capable of binding to DNA segments which include the sterol regulatory element SRE-1 (SEQ ID NO:27). SREBP is called a binding "protein" for simplicity. It will be understood that this term is not limited to a single polypeptide, but rather describes the SRE-1-binding activity present within a composition, which may result from certain domains of a polypeptide, the combined actions of one or more polypeptides, combinations of polypeptides and known transcription factors and/or multienzyme complexes, and the like.

In the present context, SRE-1 is used to refer to a "functional SRE-1 sequence". Such functional sequences are those which are capable of promoting transcription and expression of sterol-responsive genes. These may be native SRE-1 sequences, such as the sequence found upstream of any mammalian LDL receptor gene, or may be mutant SRE-1 sequences which are nonetheless capable of promoting sterol-responsive gene transcription. An SRE-1 element "capable of promoting sterol-responsive gene transcription" refers to an element which, when located upstream (i.e., 5') from and proximal to a transcription initiation site of a structural gene, serves to confer a sterol-responsive transcriptional capability to the gene. This means that significant gene transcription is promoted in the absence of sterols, but that little or no transcription is allowed in the presence of sterols. The identification, preparation and use of SRE-1 sequences is described in detail in U.S. patent application Ser. No. 07/425,852, incorporated herein by reference.

Protein Compositions

Important aspects of the present invention concern purified protein compositions, free from the environment in which it may naturally occur in intact cells, comprising a DNA binding protein which is isolatable from mammalian cell nuclei and is capable of binding to a DNA segment comprising the sterol regulatory element SRE-1 (SEQ ID NO:27). In certain embodiments, the invention concerns substantially purified SREBP. Regardless of the degree of purity, the protein compositions may be further defined as including one or more polypeptides or DNA binding domains having an apparent molecular weight on SDS/PAGE of between about 59 kD and about 68 kD. This is based upon the inventors' observation that DNA binding polypeptides having these molecular weights and described in the examples below are in fact derived from larger proteins, perhaps by proteolytic cleavage, and may in themselves represent the DNA binding domains, and transcriptionally functional domains, of larger protein(s).

The term "purified" as used herein, is intended to refer to a DNA binding protein composition wherein the SREBP is purified to any degree relative to its naturally-obtainable state, such as, relative to its purity within a nuclear extract. Generally, "purified" will refer to an SREBP composition which has been subjected to fractionation to remove various non-SREBP components, and which composition substantially retains its SRE-1 binding and/or transcription promoting activity. Where the term "substantially purified" is used, this will refer to a composition in which SREBP forms the major component of the composition, such as constituting about 50% of the proteins in the composition or more.

Although preferred for use in certain embodiments, there is no general requirement that SREBP always be provided in its most purified state. It is contemplated that less substantially purified SREBP, which nonetheless has some assayable SREBP activity, will have utility in certain embodiments. These include, for example, its use as a positive control in gel-shift assays. Partially purified SREBP may be obtained by subjecting a nuclear extract to one or a combination of the steps described above. SREBP without significant biological activity will also have utility, such as, for example, in antibody generation protocols.

Protein Purification and Assays

Various methods for quantifying the degree of purification of the SREBP will be known to those of skill in the art in light of the present disclosure. These include, for example, determining the ability of an active fraction to retard the mobility of oligonucleotides containing functional SRE-1 sequences when such 'oligos' are subjected to electrophoresis, or even, assessing the number of polypeptides within a fraction by SDS/PAGE analysis. A preferred method for assessing the purity of an SREBP fraction is to calculate the specific activity of the fraction, to compare it to the specific activity of the first fraction in which activity is measurable, and to calculate a degree of purity which may be presented as a "-fold purification number".

The actual units used to represent the amount of binding activity will, of course, be dependent upon the particular assay technique chosen to follow the purification. The present inventors prefer to use a "gel-shift" assay in which the mobility of radioactively-labelled oligonucleotides containing wild-type and mutant SRE-1 sequences is determined in the presence and absence of the protein fractions. In this system, one unit of activity corresponds to 1000 cpm of shifted probe (from 6 fmol of $^{32}$P-labelled at 40,000 cpm). However, using other assays, or even other probe preparations, the definition of a unit of activity would naturally vary.

As is generally known in the art, to determine the specific activity, one would calculate the number of units of activity per milligram of total protein. The specific activity of each purified SREBP fraction may be compared to the specific activity of the first fraction in which activity was measurable, and the "-fold purification" calculated. In preferred embodiments, the SREBP of the present invention may be purified from natural sources, such as hamster or rat liver, or preferably from human HeLa cell nuclei, to between about 200-fold and greater than 38,000-fold, and most preferably, will be provided in at least an equal to or greater than a 38,000-fold purified state.

To prepare a substantially purified DNA binding protein or SREBP composition in accordance with the present invention one may prepare an extract from mammalian cells, and preferably, a nuclear extract from HeLa cells, subject the extract to any of the fractionation procedures known to those of skill in the art, and assay the fractions to identify those containing SREBP. Fractionation steps such as ammonium sulfate precipitation, ultracentrifugation and various chromatographic procedures are preferred. Particularly advantageous fractionation steps are contemplated to include ion exchange chromatography, gel filtration chromatography, and most preferably, DNA affinity chromatography, particularly using affinity columns containing the oligonucleotide probes disclosed herein (SEQ ID NO:31 through SEQ ID NO:36).

To assay SREBP activity, the present inventors prefer to use a "gel-shift" assay in which the mobility of radioactively-labelled oligonucleotides containing wild-type and mutant SRE-1 sequences is determined in the presence and absence of the protein fractions. SREBP within a fraction will bind to functional SRE-1 sequences, but not to non-functional sequences, and will reduce or "shift" the mobility of only the oligos containing functional SRE-1. In this system, one unit of activity corresponds to 1000 cpm of shifted probe.

The present invention encompasses a significant advance over the prior art in that it advantageously provides 9 mutant, but transcriptionally-functional, SRE-1 promoters which have been shown to be positive for sterol-regulated transcription (SEQ ID NO:2 through SEQ ID NO:4, SEQ ID NO:10, and SEQ ID NO:15 through SEQ ID NO:19, respectively), and 9 non-functional mutants which have been shown to abolish transcription (SEQ ID NO:5 through SEQ ID NO:9 and SEQ ID NO:11 through SEQ ID NO:14, respectively). The invention includes both reporter gene plasmids and oligonucleotide probes containing these 18 promoter sequences (SEQ ID NO:2 through SEQ ID NO:19), which may be used for transfection and reporter gene expression studies and for gel-shift assays, respectively, to enable the unambiguous identification of SREBP.

The most preferred plasmids are those containing two copies of Repeat 2+3 (SEQ ID NO:24) (with the transcriptionally-functional or non-functional sequences), operatively linked to a TATA box and the reporter gene CAT. The most preferred radiolabeled probes are 94 bp in length and contain two copies of Repeat 2+3 (SEQ ID NO:24) (with the transcriptionally-functional or non-functional sequences), flanked by restriction sites. However, the precise nature of the plasmids and oligonucleotide probes is not critical so long as they contain a functional or non-functional SRE-1 sequence as defined herein.

Now that the functional and non-functional SRE-1 sequences have been defined by the present inventors, such sequences, e.g., any of the 18 specific probes disclosed herein (SEQ ID NO:2 through SEQ ID NO:19) may be straightforwardly used in gel-shift assays to identify SREBP, which has the capacity to discriminate between the functional and non-functional sequences. In purifying SREBP from mammalian cell nuclei, one would generally employ at least one probe to which SREBP specifically binds and at least one non-functional SRE-1 probe which SREBP does not significantly bind. Most preferably, the use of a panel of three probes, termed H, M and *, is preferred as the inventors discovered these to be the most suitable for routinely assaying SREBP activity and for discriminating between SREBP and other nuclear DNA binding proteins. Probe H includes a human repeat 2+3 sequence (SEQ ID NO:24) and is transcriptionally functional; probe M includes a mouse repeat 2+human repeat 3 sequence (SEQ ID NO:21 & SEQ ID NO:23) and is also transcriptionally functional; whereas probe * includes a mutation in repeat 2 that renders it transcriptionally non-functional (SEQ ID NO:14).

The purification method disclosed herein below contains several steps and represents the best method presently known by the inventors to prepare a substantially purified DNA binding protein or SREBP composition. This method is currently preferred as it results in the substantial purification of SREBP, as assessed by SRE-1 binding which precisely correlates with SRE-1 functionality, in yields sufficient for further characterization and use. This preferred mode of SREBP purification involves the execution of certain purification steps in the order described hereinbelow. However, as is generally known in the art, it is believed that the order of conducting the various purification steps may be changed, or that certain steps may be omitted or other steps added, and still result in a suitable method for the preparation of a substantially purified DNA binding protein or SREBP composition.

Other methods for preparing SREBP are also contemplated and fall within the scope of the present invention. One method involves preparing polyclonal or monoclonal antibodies having binding affinity for SREBP and using such antibodies in immunoabsorbent protocols to purify SREBP, for example, using an antibody affinity column.

Another advantageous method involves preparing a DNA segment which encodes SREBP, such as a cDNA or genomic fragment, expressing the DNA in a recombinant host cell and thus obtaining a "recombinant" version of SREBP. DNA segments which encode SREBP may be obtained free from total genomic DNA by any of the cloning methods known to those of skill in the art, such as, for example, expression cloning using antibodies or cloning using oligonucleotide probes designed from a knowledge of SREBP peptide sequences.

The SREBP of the present invention is contemplated to have utility as the central component in screening assays to identify candidate substances capable of promoting LDL receptor expression. However, SREBP may also be employed in a variety of other embodiments. These include, for example, in immunization regimens to prepare SREBP-specific antibodies, which may then be used in SREBP purification, SREBP cloning, or to further probe the structure, function, localization and mechanism of action of SREBP. SREBP may be used to obtain protein or peptide sequence information, for use in oligonucleotide synthesis and in SREBP cloning, or Southern or Northern blotting, or to identify and/or clone related proteins. SREBP may also be used to increase the production of any recombinant protein expressed from an SRE-1-including promoter in host cells cultured without sterols, in antisense protocols, and even to promote gene expression in hypocholesterolemic animals or in normal animals at times of low sterol levels.

Candidate Substance Screening Assays

This invention also concerns methods for conveniently evaluating candidate substances to identify compounds capable of stimulating SRE-1-mediated transcription, and hence, capable of promoting LDL receptor expression. As an increase in the number of LDL receptors at the surface of a cell allows plasma LDL levels to be reduced, any positive substances identified by the assays of the present invention will be potential LDL-cholesterol lowering drugs.

SREBP functions to bind SRE-1 DNA sequences and to promote transcription and gene expression. Therefore, the identification of an agent which promotes SREBP binding to such specific DNA sequences would be a first step towards developing a new therapeutic product for use in treating hypercholesterolemia. Various assays are contemplated as a means to search for agents which increase SREBP binding to DNA, i.e., which increase this protein's affinity.

The basis of such assays rests in mixing relatively purified SREBP-containing compositions and SRE-1 DNA segments and allowing them to form a specific bound complex which may be separated from the free components. A positive candidate substance would be one that acted to increase the amount of protein:DNA complex formed, or one that increased the stability of the complex once formed. Generally, one of the unbound species, either the protein or DNA, would be specifically labeled prior to beginning the assay in order to quantitate the amount of bound complex later formed. Radioactive or enzymatic labels may be employed, or the protein portion of the complex may be detected by means of an antibody directed against the protein.

Various forms of DNA:protein binding assays suitable for use in accordance with the present invention will be known to those of skill in the art in light of the present disclosure. These include, for example, filter-binding and microtiter plate-type assays which can all be performed in an automated or semi-automated manner to enable analysis of a large number of candidate substances in a short period of time.

Further candidate substance screening methods of the invention are based upon cellular assays in which candidate substances are screened for their ability to stimulate SRE-1-mediated transcription and gene expression, and particularly, reporter gene expression. The preferred cellular candidate substance screening assays comprise preparing a recombinant plasmid including a reporter gene, preferably a CAT gene or luciferase gene, under the transcriptional control of a functional SRE-1 sequence and introducing the plasmid into a recombinant host cell, such as a monkey CV-1 cell. The host cell is then cultured under conditions effective to allow expression of the reporter gene, which expression is measured, and then the cell is contacted with the candidate substance and the new level of reporter gene expression is measured. An increase in reporter gene expression in the presence of the candidate substance is indicative of a candidate substance capable of stimulating SRE-1-mediated transcription.

Still further embodiments of the invention concern methods to assay for candidate substances capable of stimulating SRE-1-mediated gene transcription even in the presence of sterols. These assays may be employed as a first screen, or a second screen to further analyze the properties of candidate substances which tested positive in earlier DNA binding or cellular assays. The sterol-responsive cellular screening method involves culturing the host cell in the presence of sterols and then adding the candidate substance, wherein an increase in reporter gene expression is indicative of a substance capable of stimulating SRE-1-mediated transcription even in the presence of sterols. As a practical manner, it is generally preferred to first measure gene expression without sterols, then to add sterols and to measure the "sterol-suppressed expression" and then to add the candidate substance and to test for increased reporter gene expression relative to the sterol-suppressed expression levels.

It will, of course, be understood that all the screening methods of the present invention are useful in themselves notwithstanding the fact that effective candidates may not be found, since it would be a practical utility to know that SRE-1 positive stimulators and/or sterol antagonists do not exist. The invention consists of providing methods for screening for such candidates, not in finding them.

Probes and Plasmids

In addition to purified proteins and screening assays, the present invention also encompasses various other compositions. For example, in certain embodiments it provides DNA segments, free from total genomic DNA, which encode SREBP; polyclonal or monoclonal antibodies having binding affinity for SREBP; affinity columns containing such antibodies; and DNA affinity columns containing functional or non-functional SRE-1 sequences.

In still further embodiments, the invention concerns oligonucleotide probes, recombinant plasmids and recombinant host cells, such as monkey CV-1 cells, incorporating a recombinant plasmid. Both the plasmids and probes of the present invention will generally include a transcriptionally-functional or non-functional SRE-1 sequence, in combination with a functional, i.e., wild type, Repeat 3 sequence (SEQ ID NO:23) from the LDL receptor gene. The probes and plasmids may also variously include multiple copies of the SRE-1 (Repeat 2, SEQ ID NO:22) and/or Repeat 3 sequences (SEQ ID NO:23).

Transcriptionally-functional SRE-1 sequences include the wild type sequences found within mammalian LDL receptor repeat 2 sequences (for example, SEQ ID NO:1, SEQ ID NO:20, SEQ ID NO:21), and also mutant promoters which remain positive for sterol-regulated transcription. Both the functional and non-functional versions have utility as they act as positive and negative elements by which to identify SREBP. The most preferred plasmids and probes are those which contain two copies of Repeat 2+3 (SEQ ID NO:24) (with the transcriptionally-functional or non-functional sequences), although the whole range of constructions described herein will have utility.

The plasmids will generally further comprise a TATA box sequence positioned downstream from the repeat 2 (SRE-1) (SEQ ID NO:22) and repeat 3 (SEQ ID NO:23) sequences and a reporter gene, preferably a CAT gene, positioned downstream from said TATA box sequence. The probes will also likely include flanking sequences which may be present due to the molecular biological methods, such as PCR, employed for their preparation. The probes will also preferably incorporate a readily-detectable label, such as a radioactive label, for example, $^{32}$P. The probes termed H, M and *, are particularly preferred for use in assays during SREBP purification.

| ABBREVIATIONS | |
|---|---|
| bp = | base pair |
| CAT = | chloramphenicol acetyltransferase |
| DTT = | dithiothreitol |
| HMG CoA = | 3-hydroxy-3-methylglutaryl coenzyme A |
| LDL = | low density lipoprotein |
| NP-40 = | Nonidet P-40 |
| PCR = | polymerase chain reaction |
| SRE-1 = | sterol regulatory element-1 |
| SREBP = | sterol regulatory element-1 binding protein. |

BRIEF DESCRIPTION OF THE DRAWINGS

FIG. 1. Plasmid constructs containing SRE-1 elements (Repeat 2+3) of LDL receptor promoter inserted into E1b TATA-CAT vector.

FIG. 1A, boxed sequences [2] (SEQ ID NO:22) and [3] (SEQ ID NO:23) refer to human LDL receptor gene promoter sequences −68 to −53 (repeat 2) and −52 and −37 (repeat 3) relative to the major in vivo RNA initiation site (Smith et al., 1990). The boxed sequence [2] [3] is represented as SEQ ID NO:24. The mutant sequence [2*] [3] contains the 4-bp mutation shown in lower case letters and is designated as SEQ ID NO:25.

FIG. 1B, a portion of the DNA sequence of E1b TATA-CAT vector showing the SalI insertion site for LDL receptor SRE-1 promoter elements. The sequence is designated SEQ ID NO:26. The single underline denotes the SalI site; the single overline denotes the PstI cloning site; the boxed sequence denotes the adenovirus E1b TATA sequence; and the double underline denotes the initiation codon of the CAT gene.

FIG. 2. Expression of CAT activity under control of LDL receptor promoter elements in transfected CV-1 cells. CV-1 cells were transiently transfected with the E1b TATA-CAT plasmid containing the indicated LDL receptor promoter element. After incubation for 48 hours in the absence or presence of 10 μg/ml cholesterol plus 1 μg/ml 25-hydroxycholesterol, the cells were harvested for measurement of CAT activity as described hereinbelow. The acetylated forms of [$^{14}$C]chloramphenicol (1-AcCM, 3-AcCM and 1,3-AcCM) were separated from unreacted [$^{14}$C]chloramphenicol (CM) by thin layer chromatography and detected by autoradiography. The autoradiograms were exposed for three days to allow visualization of the low expression of the LDL receptor (LDLR) construct. Plasmid J, the authentic HMG CoA synthase promoter (−550 to +35) fused to CAT, is included for comparative purposes.

FIG. 3. Single point mutation analysis of Repeat 2 of LDL receptor promoter in transfected CV-1 cells.

FIG. 4. Single point mutation analysis of Repeat 2 of LDL receptor promoter as assessed in vitro by gel mobility shift assay (FIG. 4A, lower panel) and in vivo by transient transfection in CV-1 cells (FIG. 4B, upper panel). As was indicated in the description of FIG. 3, the sequence in upper case letters is designated SEQ ID NO:1. The mutant sequences which each contain the sequence of SEQ ID NO:1 with the exception, in each case, of a single mutation indicated by the lower case letters are designated as SEQ ID NO:2 through SEQ ID NO:19, respectively.

FIG. 5. Gel mobility shift assays of HeLa cell SREBP after various steps of purification.

FIG. 6. Superdex 200 chromatography of SREBP. The 40% ammonium sulfate fraction (Step 3) was subjected to gel filtration on a Superdex 200 26/60 column as described hereinbelow.

FIG. 6A (Top Panel). Aliquots of each fraction were assayed for protein content by measurement of absorbance at 280 nm. The column was calibrated with Bio-Rad molecular weight markers containing thyroglobulin (670 kDa), aldolase (158 kDa), and ovalbumin (44 kDa). Arrows denote the positions of elution of the markers.

FIG. 6B (Bottom Panel). An aliquot (2 μl) of every other fraction was assayed for SREBP activity by the standard gel shift assay using the three $^{32}$P-probes described in FIG. 5. Arrow denotes the $^{32}$P-probe containing SREBP bound to one site. The gel was exposed for 2 hours.

FIG. 7. Purification of SREBP by DNA affinity chromatography.

Arrows denote the $^{32}$P-probes containing SREBP bound to one or two sites.

FIG. 8. Purification of SREBP on second SRE-1 DNA affinity column. Active fractions from the 1M KCl eluate from DNA affinity Column B (Step 6) were pooled, dialyzed against Buffer B containing 150 mM KCl and 0.1% NP-40, applied to two sequential mutant DNA affinity columns (Column A, SEQ ID NO:31 and SEQ ID NO:32) followed by one SRE-1 DNA affinity column (Column C, SEQ ID NO:35 and SEQ ID NO:36), and eluted as described hereinbelow in Example 2.

Figure 8B:
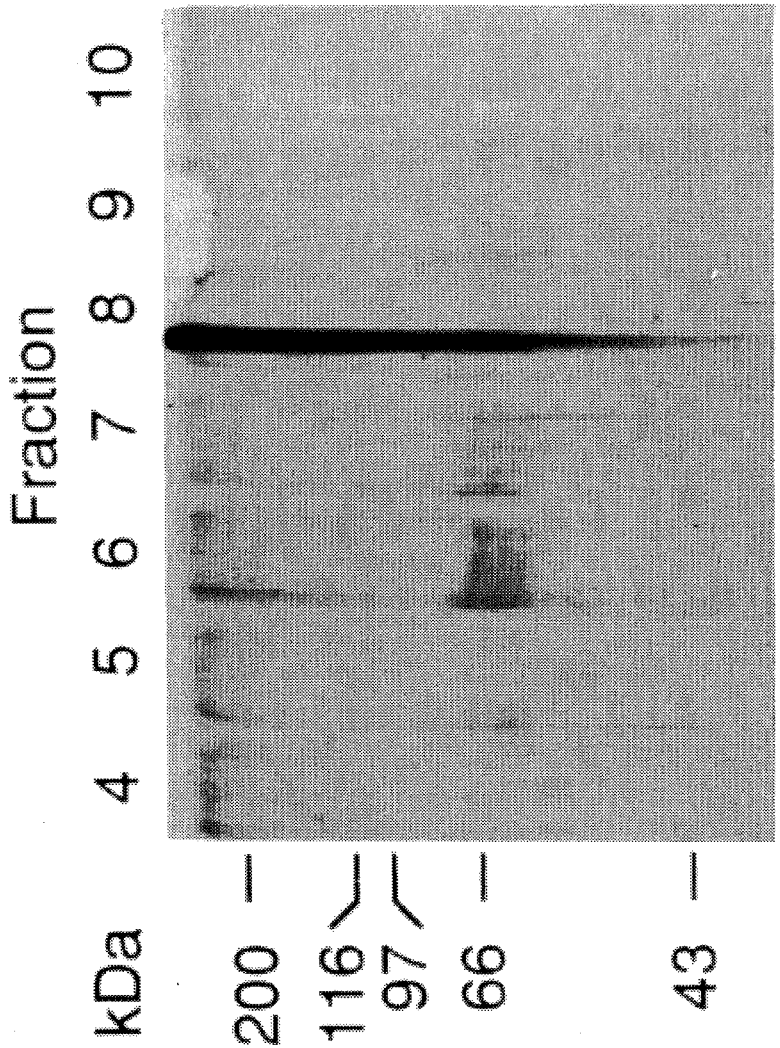
Figure 8A:
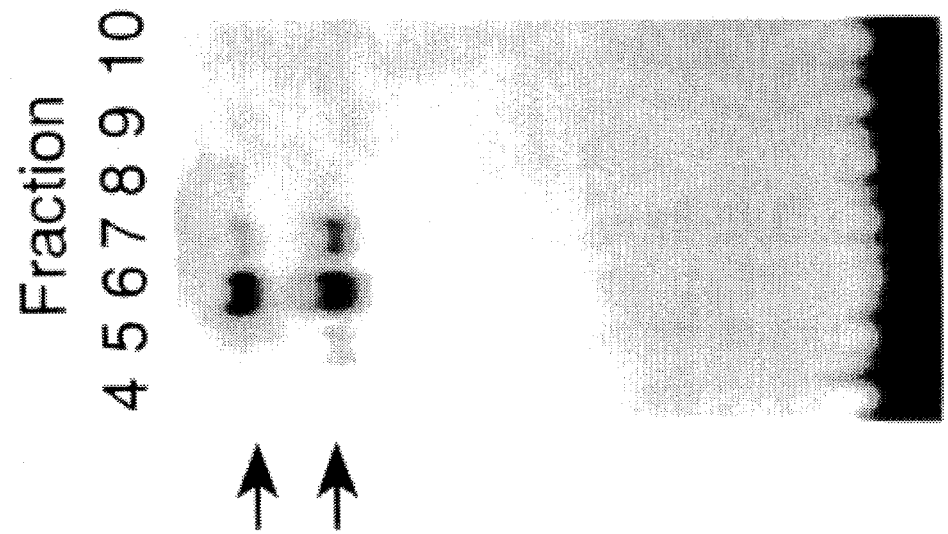

FIG. 8A (Left Panel). Aliquots (2 µl) of the stepwise NaCl elution from Column C were assayed for SREBP activity by the standard gel shift assay using $^{32}$P-probe H (see FIG. 5). The gel was exposed for 8 hours without intensifying screen. Arrows denote the $^{32}$P-probe containing SREBP bound to one or two sites.

FIG. 8B (Right Panel). Aliquots (20 µl) of the same fractions were subjected to electrophoresis on an 8% SDS-polyacrylamide minigel. The protein bands were detected by silver staining.

FIG. 9. Glycerol gradient sedimentation of purified SREBP. The peak fraction from the second SRE-1 DNA affinity column (Step 8) was loaded directly on the top of a 4.5 ml 10%–30% glycerol gradient and centrifuged as described in Example 2.

Figure 9B:
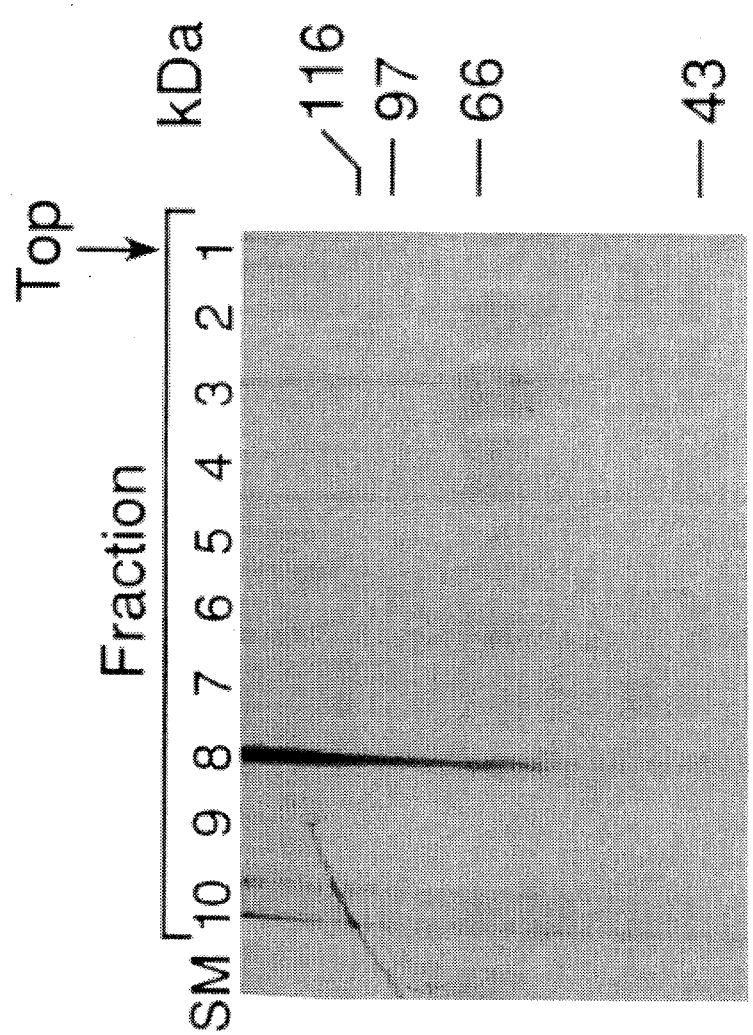
Figure 9A:
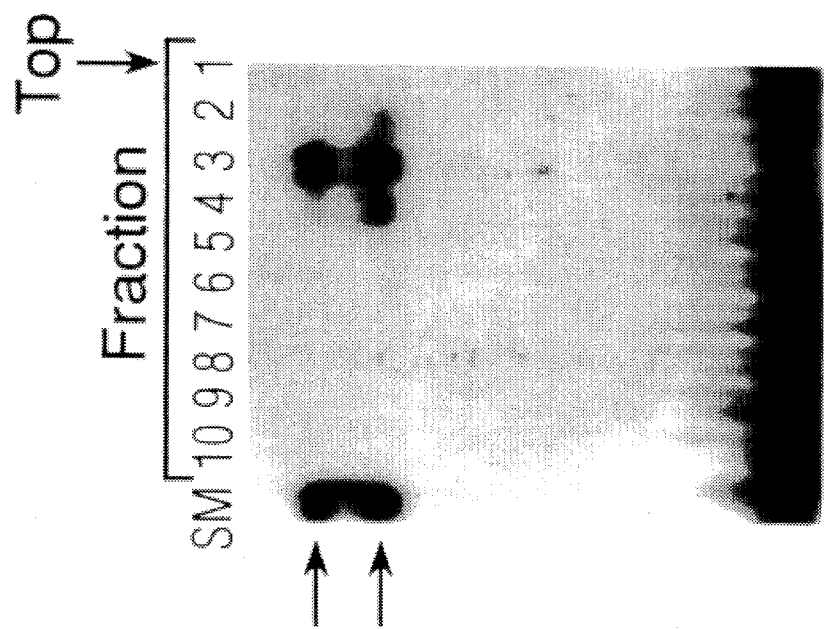

FIG. 9A (Left Panel). Aliquots (2 µl) of each fraction were assayed by the standard gel shift assay using $^{32}$P-probe H (see FIG. 5). The gel was exposed for 2 hours. Arrows denote the $^{32}$P-probe containing SREBP bound to one or two copies of SREBP.

FIG. 9B (Right Panel). Aliquots (20 µl) of the same fractions were subjected to electrophoresis on an 8% SDS-polyacrylamide minigel, and the proteins were detected by silver staining. SM, starting material.

Figure 10:
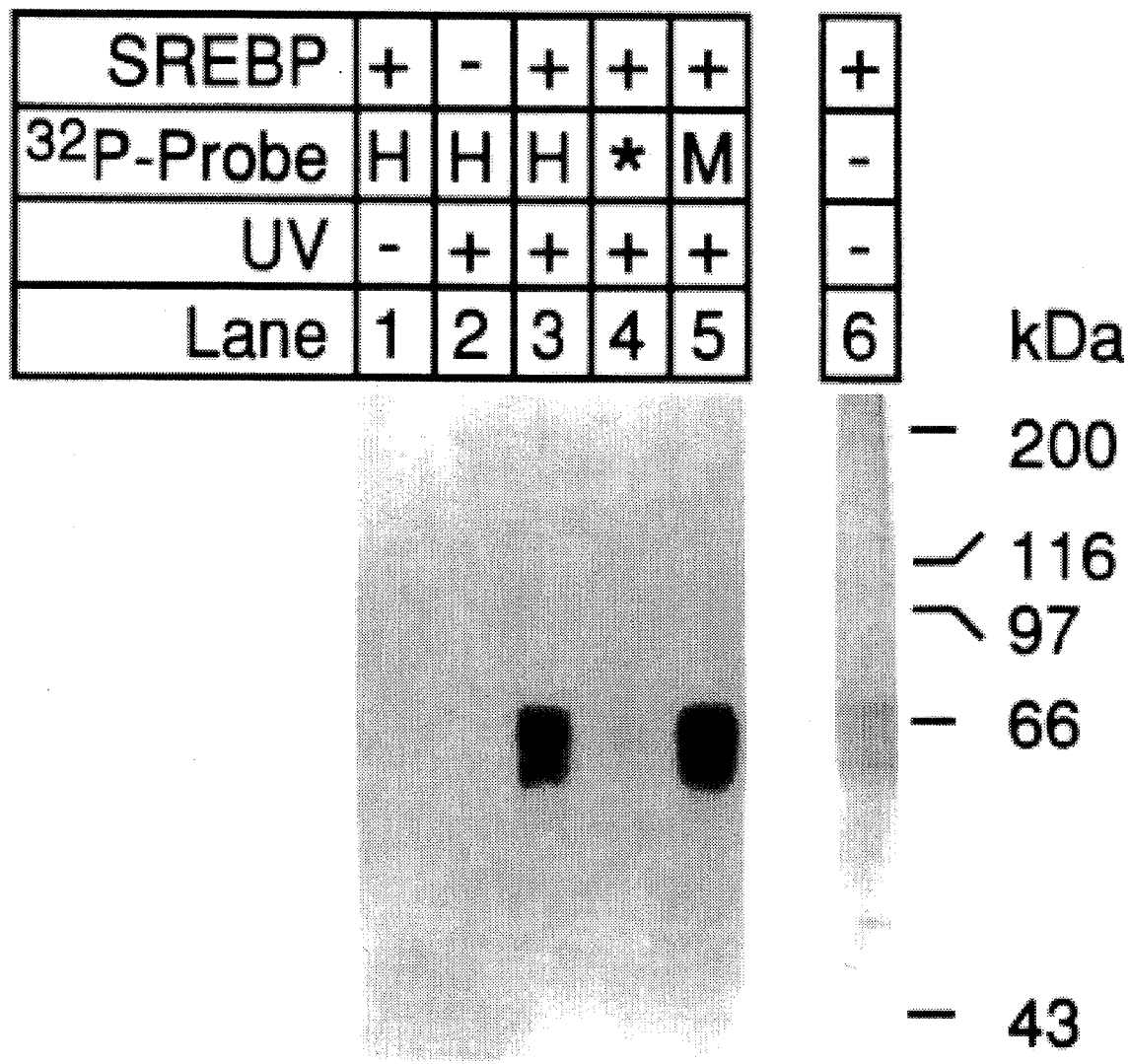

FIG. 10. Photoaffinity labeling of SREBP. Aliquots of partially purified SREBP (lanes 1–5, protein from Step 6 at 4 µg/lane) were incubated with the indicated $^{32}$P-labeled, 5'-bromo-dUTP-substituted probe and subjected to UV crosslinking as described in Example 2. After nuclease digestion, the samples were subjected to electrophoresis on an 8% SDS polyacrylamide gel. Lanes 1–5, autoradiogram of the gel after exposure to X-ray film for 48 hours at −80° C. with an intensifying screen. Lane 6, silver stain of purified SREBP (20 ng protein from Step 8) that was subjected to electrophoresis on the same gel adjacent to the samples in lanes 1–5. See FIG. 5 for description of probes H, M, and *.

Figure 11:
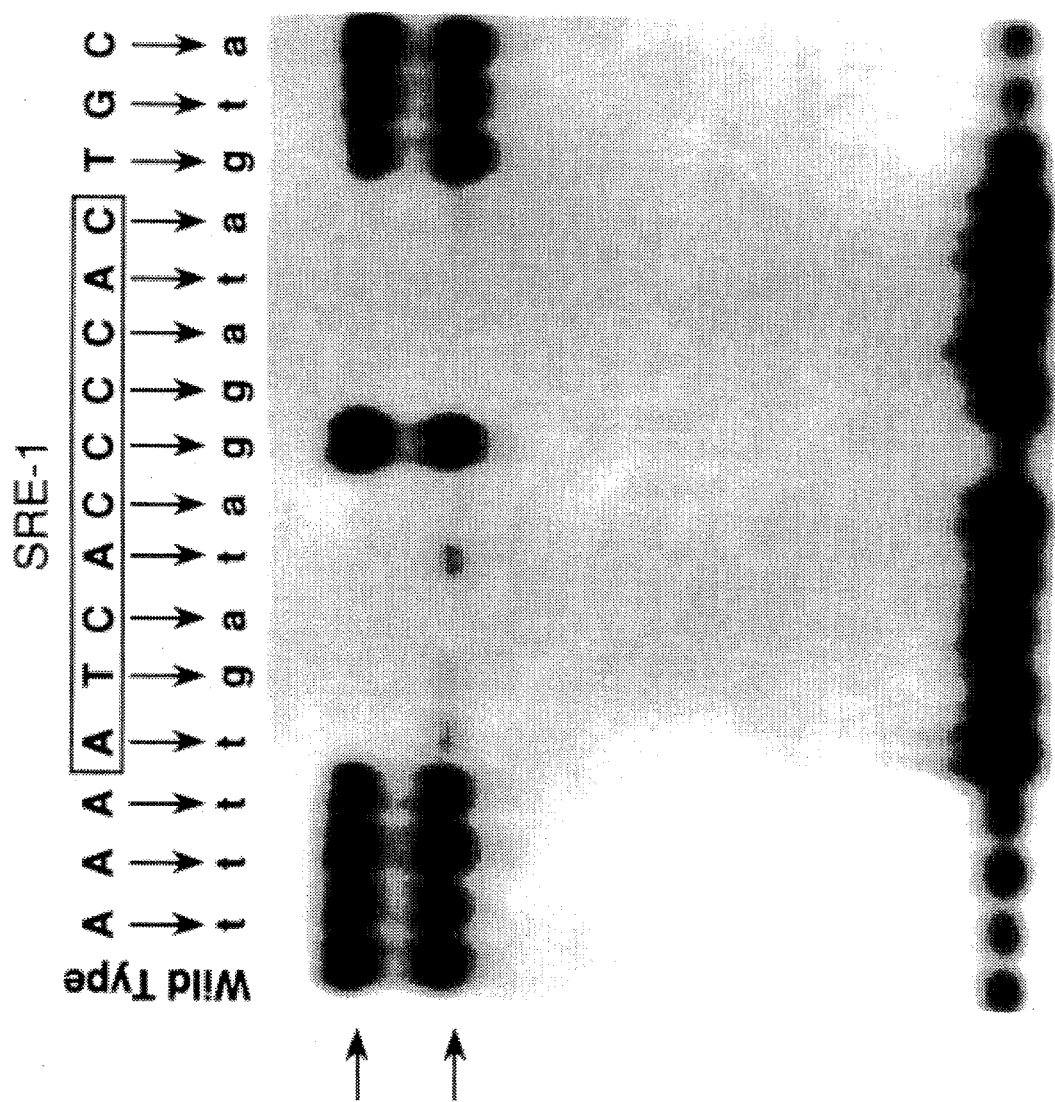

FIG. 11. Binding of purified SREBP to wild-type and mutant forms of Repeat 2. Aliquots (~1 ng) of purified SREBP (Step 8) were incubated in the standard gel shift assay with the indicated wild-type or mutant $^{32}$P-labeled, PCR-derived DNA probe of 94 bp in length. Each $^{32}$P-probe contained two tandem copies of Repeats 2+3 with the indicated point mutation in both copies of Repeat 2. Probes were prepared as described in Example 1. The sequence in upper case letters is designated SEQ ID NO:22. The mutant sequences which each contain the sequence of SEQ ID NO:22 with the exception, in each case, of a single mutation indicated by the lower case letters are designated as SEQ ID NO:2 and SEQ ID NO:17, respectively. The 10-bp sequence of SRE-1 (SEQ ID NO:27) in Repeat 2 is boxed. The gel was exposed for 2 hours. Arrows denote the $^{32}$P-probe containing SREBP bound to one or two sites of Repeat 2.

Figure 12:
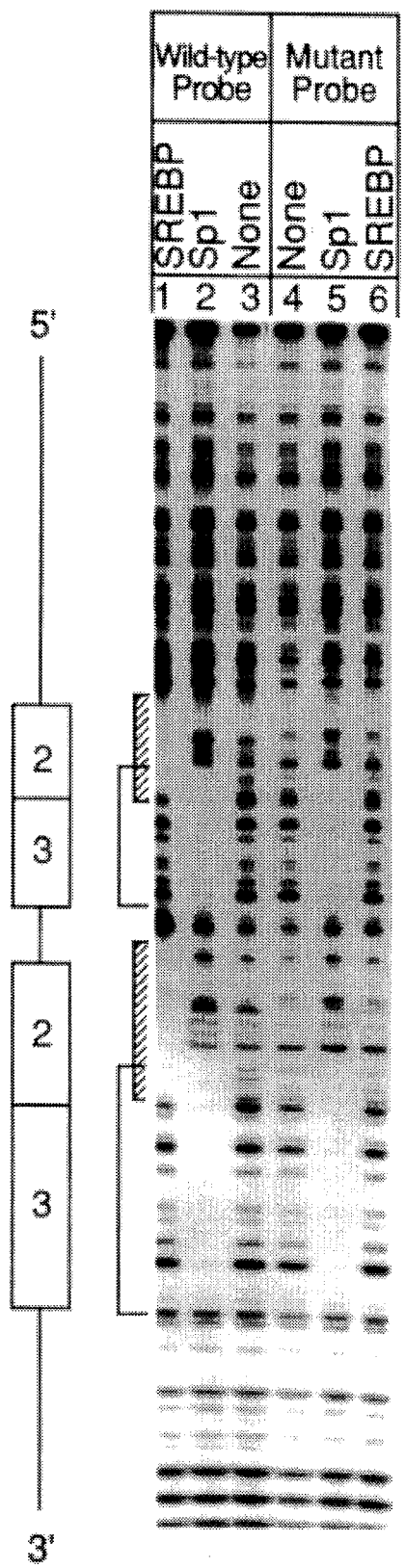

FIG. 12. DNaseI footprint of LDL receptor promoter elements by SREBP and Sp1. A 239-bp DNA fragment from Plasmid K corresponding to wild-type Probe H in gel shift studies (lanes 1–3) or Plasmid X corresponding to mutant Probe * (lanes 4–6) was end labeled with $^{32}$P on the noncoding strand as described in Example 2. The $^{32}$P-fragment (2 fmol, ~$10^4$ cpm) was incubated for 15 minutes at room temperature with one of the following proteins: none, lanes 3 and 4; 10 µg of partially purified SREBP from Step 6 (lanes 1 and 6); and 5 footprint units of purified Sp1 (lanes 2 and 5). After digestion with 40 ng DNaseI for 1 minute at room temperature (Briggs et al., 1986), each reaction mixture was stopped and subjected to electrophoresis on a 6% denaturing gel. The gel was exposed to X-ray film for 12 hours at −70° C. with intensifying screen. The locations of Repeat 2 and Repeat 3 in the $^{32}$P-DNA fragment are indicated at the left. Brackets denote the extent of the protected region (footprint) by SREBP (hatched) or Sp1 (open).

Figure 13A:
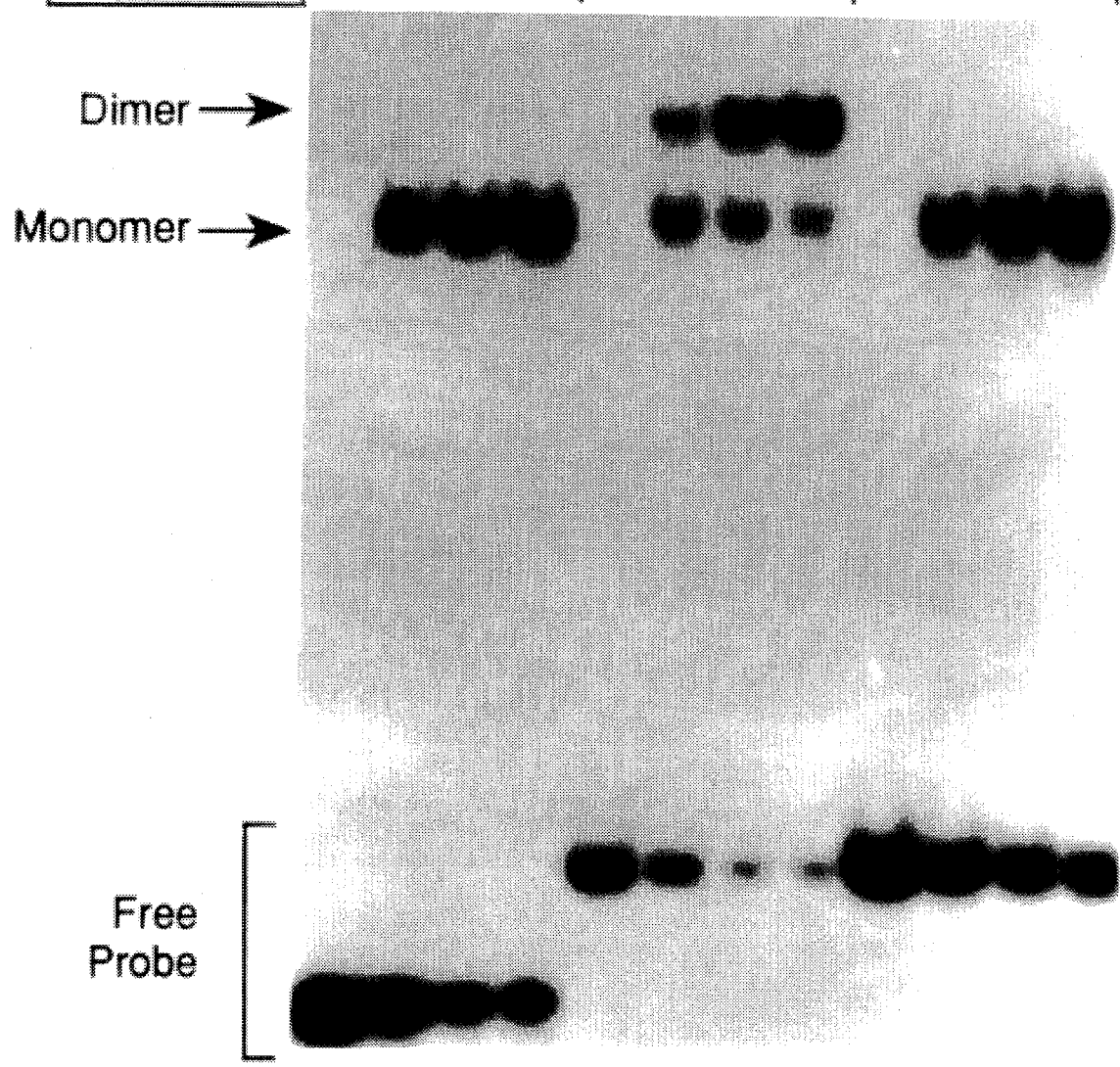
Figure 13B:
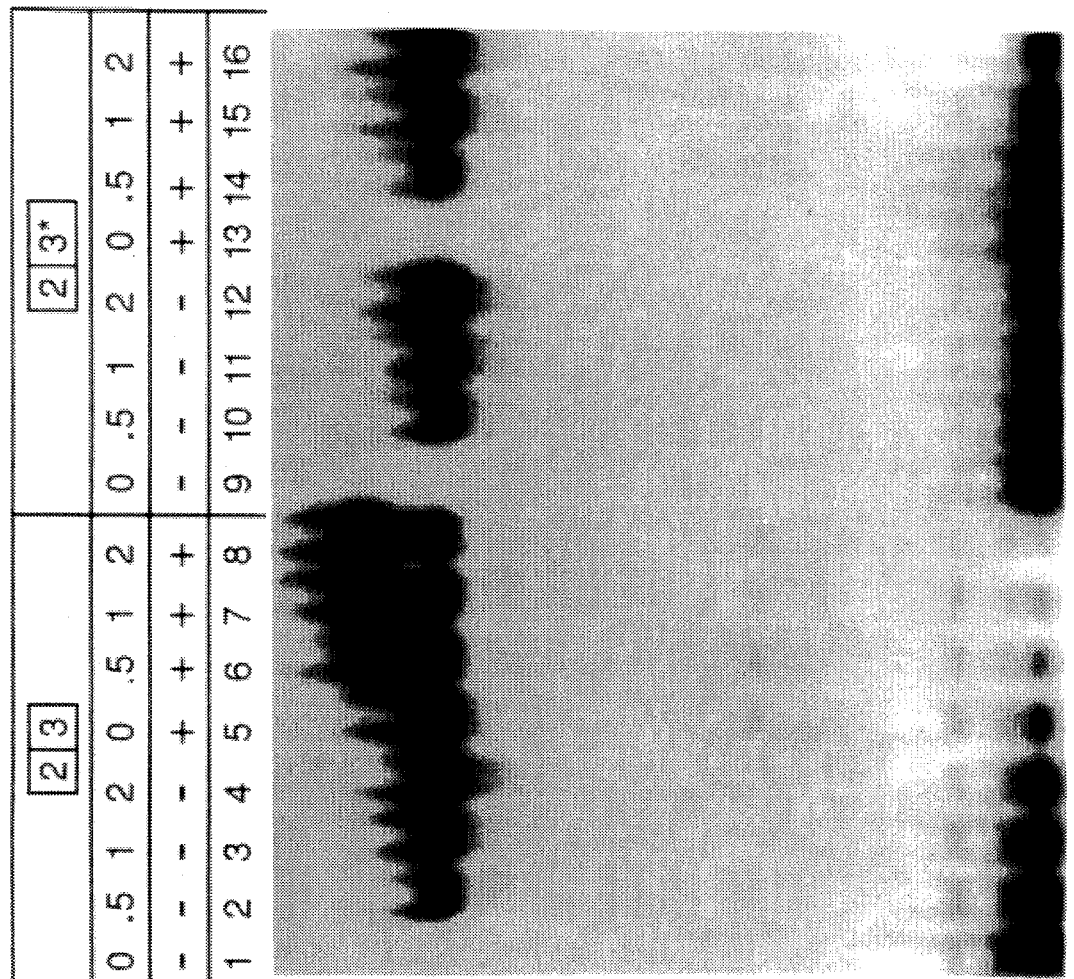

FIG. 13 consists of FIG. 13A and FIG. 13B. Binding of SREBP to oligonucleotides containing one or two copies of SRE-1.

FIG. 13A (Panel A). The indicated amount of affinity purified SREBP (Step 6) was incubated in the standard gel shift assay with one of the following $^{32}$P-probes: lanes 1–4, 12 fmol ($8\times10^4$ cpm) of $^{32}$P-probe H (see FIG. 5) digested with SalI to yield a 45-bp double-stranded fragment containing one copy of Repeat 2+3 and a 5' overhang of 4 nucleotides; lanes 5–8, 6 fmol ($4\times10^4$ cpm) of $^{32}$P-probe H containing two tandem copies of Repeat 2+3; lanes 9–12, 12 fmol ($8\times10^4$ cpm) of a PCR-generated fragment corresponding to nucleotides −103 to −38 in the human LDL receptor promoter that contains one copy of Repeat 1+2+3 (Brown & Goldstein, 1986). The gel was exposed for 1 hour. Arrows denote the $^{32}$P-probe containing SREBP bound to one or two sites.

FIG. 13 B (Panel B). The indicated amount of affinity purified SREBP (Step 8) in the absence (−) or presence (+) of 1 footprint unit of purified Sp1 was incubated in the standard gel shift assay except that the oligonucleotide competitor (mutant Repeat 2+wild-type Repeat 3 sequence) was omitted. The following $^{32}$P-probes were used: lanes 1–8, 12 fmol ($8\times10^4$ cpm) of $^{32}$P-probe H (see Panel A); lanes 9–16, 12 fmol ($8\times10^4$ cpm) of a $^{32}$P-labeled, PCR-generated 45-bp double-stranded fragment containing one copy of wild-type Repeat 2 followed by one copy of a mutant Repeat 3 that bears two C→T substitutions that eliminate Sp1 binding. The gel was exposed for 40 minutes. Arrows denote the $^{32}$P-probe containing bound SREBP and/or Sp1 as indicated.

Figure 14:
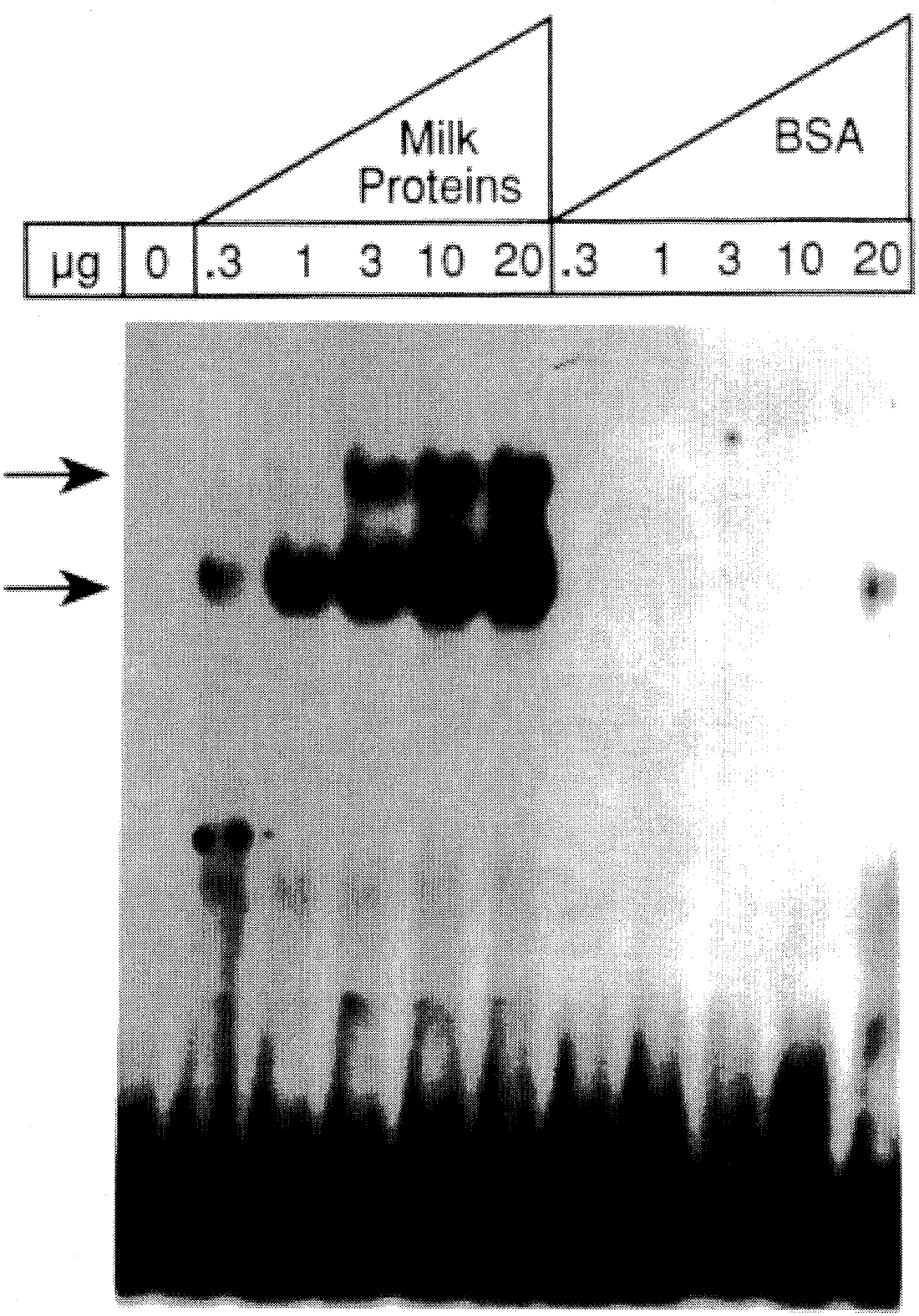

FIG. 14. Activation of SREBP by milk proteins. An aliquot (~0.14 µg) of affinity purified SREBP (Step 6) was incubated in the standard gel shift assay with $^{32}$P-labeled probe H (see FIG. 5) in the presence of the indicated amount of either milk proteins or bovine serum albumin (BSA, Fraction V; Sigma). The gel was exposed for 4 hours. Arrows denote the $^{32}$P-probe containing SREBP bound to one or two sites.

DETAILED DESCRIPTION OF THE PREFERRED EMBODIMENTS

A. Genetic Control Systems

In the 32 years since Jacob and Monod first proposed the lac operon model and the concept of messenger RNA (Jacob et al., 1961), the structure and function of a number of prokaryotic operons has been elucidated in elegant detail.

For example, it has been shown that transcriptional control of structural genes in various operons reside in upstream (i.e., 5' with respect to the structural genes) regulatory regions. In the lac operon, a regulatory gene produces a protein repressor that interacts with an "operator" to prevent transcription initiation of the structural gene. Metabolic inducers bind to the repressor and thereby induce transcription by preventing the binding of the repressor to the operator. Additionally, there is a promoter site P, upstream of the operator and downstream of the regulatory gene, which serves as an RNA polymerase binding site.

Studies on the lac operon further have led to the discovery and elucidation of the mechanism of prokaryotic catabolic suppression. In *E. coli* it is found that the presence of glucose in the growth medium serves to prevent expression of gluconeogenic pathways, including the lac operon and its associated structural genes.

In contrast to prokaryotic systems, much less is presently known about control mechanisms, and particularly feedback suppression, in eukaryotic systems. Positively-regulated systems in which hormones, metabolic inducers, and developmental factors increase transcription of genes are somewhat better understood. In these systems, positive inducing agents are thought to activate or form complexes with proteins that stimulate transcription by binding to short sequences of 10 to 20 base pairs (bp) in the 5'-flanking region of the target gene. The sequences for the glucocorticoid, metal and interferon regulatory elements (GRE, MRE, and IRE, respectively) have been reported (Yamamoto, 1985; Stuart et al., 1984; Goodbourn et al., 1986).

More recently, other DNA segments which are capable of conferring control capability to known genes in eukaryotic systems have been identified, including the sterol regulatory element-1 (SRE-1) associated with the low density lipoprotein (LDL) receptor. Although this represents a significant advance, the protein factor which binds to SRE-1 and stimulates transcription has yet to be identified.

The identification of the SRE-1 binding protein would be an important step towards elucidating the mechanisms of eukaryotic gene control, and would also provide biomedical science with a powerful tool by which to regulate specific gene expression. Such a development would lead to numerous useful applications in the pharmaceutical and biotechnological industries. Although many applications are envisioned, one particularly useful application would be as the central component in screening assays to identify new classes of pharmacologically active substances which may be employed to manipulate, and particularly, to promote, the transcription of structural genes such as the LDL receptor gene.

An SRE-1 binding protein or transcription factor would thus be of great use in identifying agents to combat hypercholesterolemia. A cholesterol-lowering agent would act to promote the cellular production of LDL receptors, which would in turn serve to lower plasma LDL-cholesterol levels by increasing the cellular uptake of LDL.

B. Cholesterol Metabolism

Animal cells regulate their cholesterol content through the integration of two pathways that govern the supply of exogenous and endogenous cholesterol. Both pathways are controlled by end-product repression. Cells may obtain cholesterol through the receptor-mediated endocytosis and lysosomal hydrolysis of plasma low density lipoprotein. Cells may also increase their endogenous cholesterol production by increasing the amount of two enzymes involved in de novo cholesterol biosynthesis, namely, 3-hydroxy-3-methylglutaryl coenzyme A (HMG CoA) synthase and HMG CoA reductase.

The LDL receptor gene is the structural gene which provides for the production of the LDL receptor protein, the receptor protein responsible for the facilitated uptake of cholesterol by mammalian cells. Upstream of the coding sequences for the LDL receptor gene is the SRE-1 sequence, which provides for sterol-mediated regulation of LDL receptor gene transcription. In the relative absence of sterols within the cell, transcription of the LDL receptor gene is promoted, whereas in the presence of cholesterol, transcription is suppressed. The transcription of HMG-CoA synthase and reductase of the cholesterol biosynthetic pathway is also reduced when sterols accumulate within the cell. When sterols are depleted, transcription increases and both the uptake and synthesis of cholesterol is promoted.

Currently, there are few cholesterol-lowering drugs that are both safe and efficacious, and no drugs which are known to operate at the genetic control level, as described above. For example, aside from agents that function by sequestering bile salts in the gut and thereby increase cholesterol excretion, the principal therapeutic agent available for cholesterol lowering is Lovastatin, a drug manufactured by Merck, Co. that acts indirectly to stimulate production of LDL receptors.

Lovastatin, and other drugs in this class (Simvastatin, Pravastatin), act by inhibiting the activity of HMG CoA reductase, the rate-limiting enzyme of endogenous cholesterol synthesis. These drugs contain side chains that resemble the native substrate for HMG CoA reductase and thus competitively inhibit the activity of the enzyme. Eventually this lowers the endogenous synthesis of cholesterol and, by normal homeostatic mechanisms, plasma cholesterol is taken up by increased LDL receptor populations in order to restore the intracellular cholesterol balance.

Conceptually, HMG CoA reductase inhibitors are acting at the penultimate stage of cellular mechanisms for cholesterol metabolism. It would be most desirable if the synthesis of LDL receptor could be directly up regulated at the gene level. The up regulation of LDL receptor synthesis at the gene level offers the promise of resetting the level of blood cholesterol at a lower and clinically more desirable level (Brown et al., 1984) However, no methods exist for conveniently assaying the ability of a candidate composition to exert such an effect on the transcription of the LDL receptor gene.

C. SRE-1 Sequences and Heterologous Gene Expression

The identification, preparation and use of SRE-1 sequences is described in detail in U.S. patent application Ser. Nos. 07/033,302 (U.S. Pat. No. 4,935,363), 07/425,852, 07/532,318, 07/033,081, 07/032,134 and 07/032,130, each incorporated herein by reference. SRE-1 sequences may be employed as novel control units to direct sterol-mediated expression. Placing such sequences upstream of and sufficiently proximal to a transcription initiation site of a given gene will impart a sterol-regulated transcriptional control capability to the gene. LDL receptor gene repeat 2 and repeat 3 sequences may be advantageously used, and may be employed as multiple units, in numerous various combinations and organizations, in forward or reverse orientations, but preferably, would be located within from 0–20 nucleotides of each other.

SRE-1 control sequences may be employed to direct expression of heterologous structural genes. The precise location of the SRE-1 sequences is not particularly crucial and they may be located up to about 300 nucleotides or more from a transcription initiation site, with distances of 150, 100 and 50 nucleotides being preferred. In general, the closer the control sequences are to transcription initiation, the more pronounced and effective the control obtained.

To employ the sterol regulatory elements in the context of heterologous gene expression, one simply obtains the structural gene and attaches one or more of such control sequences upstream of a transcription initiation site. Additionally, as is known in the art, it is generally desirable to include TATA-box sequences upstream of and proximal to a transcription initiation site of the heterologous structural gene. Such sequences may be synthesized and inserted in the same manner as the novel control sequences. Alternatively, one may desire to simply employ the TATA sequences normally associated with the heterologous gene. In any event, TATA sequences are most desirably located between about 20 and 30 nucleotides upstream of transcription initiation.

Numerous methods are known in the art for precisely locating selected sequences at selected points within larger sequences. Most conveniently, the desired control sequence or sequences, or combinations of sequences, are synthesized and restriction site linker fragments added to the control sequence termini. This allows for ready insertion of control sequences into compatible restriction sites within upstream regions. Alternatively, synthesized control sequences may be ligated directly to selected regions. Moreover, site specific mutagenesis may be employed to fashion restriction sites into which control sequences may be inserted in the case where no convenient restriction sites are found at a desired insertion site.

D. SRE-1 Sequence Mutant Analyses

An important aspect of the present invention is the delineation of the essential nucleotides within the SRE-1 sequence and the identification of a nuclear protein that binds to this newly-defined target nucleotide sequence.

In order to identify and purify the physiologically relevant SRE-1 binding protein, the inventors designed and created a series of oligonucleotide probes with point mutations that either inactivated the SRE-1 or retained transcriptional activity. It was then possible to characterize the transcriptional activity of the mutant sequences in transient transfection assays. This is an advantage over previous studies of the LDL receptor promoter, using permanently transfected cell lines, which proved cumbersome for the analysis of multiple mutations (Smith et al., 1990; Sudhof et al., 1987; Dawson et al., 1988). As with other transcriptional regulatory systems (Klein-Hitpass et al., 1990; Pascal et al., 1991; Freedman et al., 1989), the activity of promoter elements in transient assays was increased by the creation of artificial promoters with multiple copies of the transcriptional element combined with novel TATA boxes.

The present inventors created an artificial sterol-dependent promoter by oligomerizing multiple copies of Repeat 2+3 in tandem and inserting them upstream of a TATA box derived from the adenovirus E1b gene (Lillie et al., 1989). The resulting vectors produced high levels of transcription in sterol-deprived cells after transient transfection. Transcription was repressed by sterols to a degree that is greater than observed with the native LDL receptor. This system allowed the inventors to define the precise nucleotides required for sterol-dependent regulation through point mutational analysis of Repeat 2. It was found that a segment of 10 nucleotides (SEQ ID NO:27) within the 16-bp Repeat 2 element (SEQ ID NO:22) is required for high level sterol-sensitive transcription activity and that mutation of any one of 9 nucleotides within this sequence markedly reduced the transcriptional activity of the SRE-1. The sole exception was the nucleotide at position 6 (the second C in the CCCC tetramer).

This information was used to design a series of oligonucleotides with point mutations that either permit or disrupt sterol-regulated transcription for use in specific gel shift assays. Using this system, a nuclear protein from HeLa cells or rat liver nuclei was identified that bound to the SRE-1 sequence in a fashion that was dependent on each of the 9 nucleotides that were required for transcription. Strikingly, the binding of this protein did not depend on a C nucleotide at the 6th position, which was also not necessary for transcriptional activity. In light of the precision of this correlation, the inventors propose that this protein, designated sterol regulatory element-1 binding protein (SREBP), is the protein required for sterol-sensitive transcription.

E. SRE-1 Binding Protein, SREBP

Another important aspect of the invention is the purification and characterization of SREBP. This proved particularly difficult as SREBP is present in trace amounts and as several abundant nuclear proteins also bind to the SRE-1 sequence and obscure the binding of SREBP. The inventors were required to identify the most discriminatory oligonucleotides, herein termed M and *, for use in the SREBP assay, and to overcome many obstacles during the initial preparation.

SREBP was purified more than 38,000-fold from nuclear extracts of human HeLa cells by ion exchange, gel filtration, and DNA affinity chromatography. SDS polyacrylamide gel electrophoresis of the purified preparation revealed a cluster of bands at 59–68 kDa, each of which bound to the SRE-1 element as revealed by crosslinking studies. This may represent multiple modifications of a single protein or several related proteins. Results from gel filtration and glycerol gradient centrifugation suggest that SREBP may exist as a multiprotein complex which dissociates during purification. Alternatively, it may be an elongated molecule that behaves anomalously on gel filtration.

The inventors contemplate that if SREBP multiprotein complexes exist, they may be formed from identical or distinct SREBP polypeptides, or that SREBP may even exist in combination with other known, or as yet unidentified proteins, in an analogous manner to that recently described for the Myc, Mad and Max transcriptional system (Ayer et al., 1993). The inventors also propose that SREBP will likely be found to be composed of more than one functional domain. Such domains may be separated, e.g., by proteolytic cleavage, into distinct domains which maintain activity—in an analogous manner to that reported by Gil et al. (1988a; 1988b).

Binding of SREBP correlated perfectly with transcriptional activity in a series of 16 sterol regulatory elements with point mutations. In the LDL receptor promoter the 10-base pair SRE-1 (SEQ ID NO:27) is embedded in a 16-base pair sequence designated Repeat 2 (SEQ ID NO:22), which is adjacent to Repeat 3 (SEQ ID NO:23), a binding site for nuclear factor Sp1. Oligonucleotides containing Repeat 2+3 (SEQ ID NO:24) bound SREBP and Sp1 as revealed by mobility shift assays. SREBP produced a DNase I footprint over the SRE-1 sequence, which was immediately adjacent to the footprint produced by Sp1. The current data are consistent with the inventors' concept that SREBP acts in concert with Sp1 to achieve high level, sterol-suppressible transcription of the gene for the LDL receptor.

The inventors contemplate that the treatment of SREBP with various agents, such as phosphatases, kinases, or even proteases, will lead to further information concerning its mode of action and regulation. It is envisioned that the genetic engineering of SREBP will ultimately be possible, and that such techniques may lead to the development of second generation SREBP capable of promoting significant LDL receptor transcription even in the presence of sterols. In this regard, the mutation of potential phosphorylation sites and/or the modification or deletion of larger segments or domains is contemplated.

F. Antibodies directed against SREBP

Antibodies, both polyclonal and monoclonal, specific for the SREBP of the present invention may be prepared using conventional immunization techniques, as will be generally known to those of skill in the art. A composition containing antigenic epitopes of the SREBP can be used to immunize one or more experimental animals, such as a rabbit or mouse, which will then proceed to produce specific antibodies against the SREBP. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with an SREBP composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to SREBP.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against SREBP. Hybridomas which produce monoclonal antibodies to the selected antigens are identified using standard techniques, such as ELISA and Western blot methods. Hybridoma clones thus identified can then be cultured in liquid media and the culture supernatants purified to provide the SREBP-specific monoclonal antibodies.

In general, both poly- and monoclonal antibodies against SREBP may be used in a variety of embodiments. For example, they may be employed in antibody cloning protocols to obtain cDNAs or genes encoding SREBP or related proteins. They may also be used in inhibition studies to analyze the effects of SREBP, or certain domains of SREBP, in cells or animals. Anti-SREBP antibodies will also be useful in immunolocalization studies to analyze the distribution of SREBP during various cellular events, for example, to determine the nuclear and/or cellular distribution during the presence or absence of sterols. A particularly useful application of such antibodies is in immunoabsorbent protocols such as may be employed to purify native or recombinant SREBP, for example, using an antibody affinity column. The operation of all such immunological techniques will be known to those of skill in the art in light of the present disclosure.

G. Molecular Cloning of SREBP

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule. Techniques such as these would also, of course, be appropriate for the production of SREBP in accordance with the present invention.

The first step in such cloning procedures is the screening of an appropriate DNA library, such as, in the present case, a mammalian DNA library. The screening procedure may be an expression screening protocol employing antibodies directed against SREBP. Alternatively, screening may be based on the hybridization of oligonucleotide probes, designed from a consideration of portions of the amino acid sequence of SREBP. After identifying an appropriate DNA molecule, it may be inserted into any one of the many vectors currently known in the art and transferred to a prokaryotic or eukaryotic host cell where it will direct the expression and production of the so-called "recombinant" version of SREBP.

It will be understood that recombinant SREBP may differ from naturally-produced SREBP in certain ways. In particular, the degree of post-translational modifications, such as, for example, glycosylation and phosphorylation, may be different between recombinant SREBP and SREBP obtained following purification from natural sources such as HeLa cells. Moreover, the recombinant SREBP may encode a protein that is larger in molecular mass than the protein that was purified as would occur if the latter underwent proteolysis during the purification process.

H. In vitro Screening Assays for Candidate Substances

Further important aspects of this invention are methods for conveniently evaluating candidate substances to identify compounds capable of stimulating SRE-1-mediated transcription. Such compounds will be capable of promoting LDL receptor expression, and thus can be said to have receptor up regulating activity. In as much as increased LDL receptor expression in the body functions to reduce plasma LDL concentrations (Brown and Goldstein, 1986), any positive substances identified by the assays of the present invention will be potential cholesterol-lowering agents or anti-hypercholesterolemic drugs. Before human administration, such compounds would be rigorously tested using conventional animal models known to those of skill in the art.

Successful candidate substances may function in the absence of added sterols, in which case the candidate compound may be termed a "positive stimulator" of SRE-1. Alternatively, such compounds may stimulate transcription in the presence of sterols, i.e., function to oppose sterol-mediated suppression, and thus may be termed "a sterol antagonist". Compounds may even be discovered which combine both of these actions. Although the antagonist class of compounds may ultimately seem to be the most desirable, compounds of either class will likely be useful therapeutic agents for use in stimulating LDL receptor production and lowering blood cholesterol in human subjects.

As SREBP is herein shown to bind to functional SRE-1 DNA sequences, one method by which to identify a candidate substance capable of stimulating SRE-1-mediated transcription is based upon specific protein:DNA binding. Accordingly, to conduct such an assay, one would prepare an SREBP protein composition and determine the ability of a candidate substance to increase SREBP binding to a DNA segment including a functional SRE-1 sequence, i.e., to increase the amount or the binding affinity of a protein:DNA complex.

This would generally be achieved using two parallel assays, one which contains SREBP and the specific DNA alone and one which contains SREBP, DNA and the candidate substance composition. One would perform each assay under conditions, and for a period of time, effective to allow the formation of protein:DNA complexes, and one would then separate the bound protein:DNA complexes from any unbound protein or DNA and measure the amount of the protein:DNA complexes. An increase in the amount of the bound protein:DNA complex formed in the presence of the candidate substance would be indicative of a candidate substance capable of promoting SREBP binding, and thus, capable of stimulating SRE-1-mediated transcription.

In such binding assays, the amount of the protein:DNA complex may be measured, after the removal of unbound species, by detecting a label, such as a radioactive or enzymatic label, which was incorporated into the original SREBP composition or SRE-1-containing DNA segment. Alternatively, one could detect the protein portion of the complex by means of an antibody directed against the protein.

Preferred binding assays are those in which either the SREBP composition or the SRE-1-containing DNA segment is bound to a solid support and contacted with the other component to allow complex formation. Unbound protein or DNA components are then separated from the protein:DNA complexes by washing and the amount of the remaining bound complex quantitated by detecting the label or with antibodies. Such DNA binding assays form the basis of filter-binding and microtiter plate-type assays and can be performed in a semi-automated manner to enable analysis of a large number of candidate substances in a short period of time. Electrophoretic methods, such as the gel-shift assay disclosed herein, could also be employed to separate unbound protein or DNA from bound protein:DNA complexes, but such labor-intensive methods are not preferred.

Assays such as those described above are initially directed to identifying positive stimulator candidate substances and do not, by themselves, address the activity of the substance in the presence of sterols. However, such positive regulators may also prove to act as sterol antagonists, and in any event, would likely have utility in transcriptional promotion, either in vitro or in vivo. Positive regulators would likely be further evaluated to assess the effects of sterols on their action, for example, by employing a cellular reporter gene assay such as those described hereinbelow.

Virtually any candidate substance may be analyzed by these methods, including compounds which may interact with SREBP, SRE-1 or protein:DNA complexes, and also substances such as enzymes which may act by physically altering one of the structures present. Examples of the former substances include sterols and sterol derivatives, and an example of the latter include phosphatase or kinase enzymes which may regulate SREBP activity. Of course, any compound isolated from natural sources such as plants, animals or even marine, forest or soil samples, may be assayed, as may any synthetic chemical or recombinant protein.

Another potential method for stimulating SRE-1-mediated transcription is to prepare a SREBP composition and to modify the protein composition in a manner effective to increase SREBP binding to a DNA segment including the sterol regulatory element SRE-1. The binding assays would be performed in parallel, similar to those described above, allowing the native and modified SREBP to be compared. In addition to phosphatases and kinases, other agents, including proteases and chemical agents, could be employed to modify SREBP. The present invention also opens the way for genetically engineering SREBP to promote LDL receptor transcription that is not suppressible by sterols. In this regard, the mutation of potential phosphorylation sites and/ or the modification or deletion of other domains is contemplated.

I. Reporter Genes and Cell-Based Screening Assays

Cellular assays are also available for screening candidate substances to identify those capable of stimulating SRE-1-mediated transcription and gene expression. In these assays, the increased expression of any natural or heterologous gene under the control of a functional SRE-1 element may be employed as a measure of stimulatory activity, although the use of reporter genes is preferred. A reporter gene is a gene that confers on its recombinant host cell a readily detectable phenotype that emerges only under specific conditions. In the present case, the reporter gene, being under the control of a functional SRE-1 element, will generally be expressed under conditions of sterol deprivation and will generally be repressed in the presence of sterols.

Reporter genes are genes which encode a polypeptide not otherwise produced by the host cell which is detectable by analysis of the cell culture, e.g., by fluorometric, radioisotopic or spectrophotometric analysis of the cell culture. Exemplary enzymes include luciferases, transferases, esterases, phosphatases, proteases (tissue plasminogen activator or urokinase), and other enzymes capable of being detected by their physical presence or functional activity. The reporter gene currently preferred is chloramphenicol acetyltransferase (CAT; Osborne et al., 1985) which may be employed with a radiolabeled substrate, or luciferase, which is measured fluorometrically.

Another class of reporter genes which confer detectable characteristics on a host cell are those which encode polypeptides, generally enzymes, which render their transformants resistant against toxins, e.g., the neogene which protects host cells against toxic levels of the antibiotic G418, and genes encoding dihydrofolate reductase, which confers resistance to methotrexate. Genes of this class are not generally preferred since the phenotype (resistance) does not provide a convenient or rapid quantitative output. Resistance to antibiotic or toxin requires days of culture to confirm, or complex assay procedures if other than a biological determination is to be made.

Other genes of potential for use in screening assays are those capable of transforming hosts to express unique cell surface antigens, e.g., viral env proteins such as HIV gp120 or herpes gD, which are readily detectable by immunoassays. However, antigenic reporters are not preferred because, unlike enzymes, they are not catalytic and thus do not amplify their signals.

The polypeptide products of the reporter gene are secreted, intracellular or, as noted above, membrane bound polypeptides. If the polypeptide is not ordinarily secreted it is fused to a heterologous signal sequence for processing and secretion. In other circumstance the signal is modified in order to remove sequences that interdict secretion. For example, the herpes gD coat protein has been modified by site directed deletion of its transmembrane binding domain, thereby facilitating its secretion (EP 139,417A). This truncated form of the herpes gD protein is detectable in the culture medium by conventional immunoassays. Preferably, however, the products of the reporter gene are lodged in the intracellular or membrane compartments. Then they can be fixed to the culture container, e.g., microtiter wells, in which they are grown, followed by addition of a detectable signal generating substance such as a chromogenic substrate for reporter enzymes.

The transcriptional promotion process which, in its entirety, leads to enhanced transcription is termed "activation." The mechanism by which a successful candidate substance acts is not material since the objective is to promote LDL receptor expression, or even, to promote LDL receptor expression in the presence of sterols, by whatever means will function to do so.

To create an appropriate vector or plasmid for use in such assays one would ligate the SRE-1-containing promoter, whether a hybrid or the native LDL receptor promoter, to a DNA segment encoding the reporter gene by conventional methods. The SRE may be obtained by in vitro synthesis or recovered from genomic DNA and should be ligated upstream of the start codon of the reporter gene. An AT-rich TATA box region should also be employed and should be located between the SRE-1 sequence and the reporter gene start codon. The region 3' to the coding sequence for the reporter gene will ideally contain a transcription termination and polyadenylation site. The promoter and reporter gene may be inserted into a replicable vector and transfected into a cloning host such as E. coli, the host cultured and the replicated vector recovered in order to prepare sufficient quantities of the construction for later transfection into a suitable eukaryotic host.

Host cells for use in the screening assays of the present invention will generally be mammalian cells, and are preferably cell lines which may be used in connection with transient transfection studies. Cell lines should be relatively easy to grow in large scale culture. Also, they should contain as little native background as possible considering the nature of the reporter polypeptide. Examples include the Hep G2, VERO, HeLa, human embryonic kidney, 293, CHO, W138, BHK, COS-7, and MDCK cell lines, with monkey CV-1 cells being particularly preferred.

The screening assay typically is conducted by growing recombinant host cells in the presence and absence of candidate substances and determining the amount or the activity of the reporter gene. To assay for candidate substances capable of exerting their effects in the presence of sterols, one would make serial molar proportions of cholesterol and/or other sterols that suppress SRE-1-mediated expression to the cells. One would ideally measure the reporter signal level after an incubation period that is sufficient to demonstrate sterol-mediated repression of signal expression in controls incubated solely with sterols, for example with 10 micrograms cholesterol/ml and 1 microgram 25-hydroxy-cholesterol/ml. Cells containing varying proportions of candidate substances would then be evaluated for signal activation in comparison to the suppressed levels.

Candidates that demonstrate dose related enhancement of reporter gene transcription or expression are then selected for further evaluation as clinical therapeutic agents. The stimulation of transcription may be observed in the absence of added sterols, in which case the candidate compound might be a positive stimulator of the SRE. Alternatively, the candidate compound might only give a stimulation in the presence of sterols, which would indicate that it functions to oppose the sterol-mediated suppression of the SRE. Candidate compounds of either class might be useful therapeutic agents that would stimulate production of LDL receptors and thereby lower blood cholesterol in patients.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Identification of the Sterol Regulatory Element-1 Binding Protein (SREBP) and Delineation of its target Nucleotide Sequence The present example reports the identification of a protein in rat liver nuclei that binds to the sterol regulatory element (SRE-1), as exemplified by SRE-1 in the promoter of the gene for the low density lipoprotein (LDL) receptor (SEQ ID NO:27). The 10-base pair SRE-1 (SEQ ID NO:27) is embedded within a 16-base pair sequence designated Repeat 2 (SEQ ID NO:22) located immediately upstream of a related sequence designated Repeat 3 (SEQ ID NO:23).

To confirm that DNA recognition by the SRE-1 binding protein (SREBP) correlates with sterol-regulated transcription, an artificial promoter was synthesized that contains two copies of wild-type or mutant Repeat 2+3 sequences immediately upstream of a TATA box from adenovirus. The synthetic promoters were inserted upstream of a reporter gene and tested for transcriptional activity in the absence and presence of sterols after transient transfection into monkey CV-1 cells. The reporter gene with two copies of the wild-type Repeat 2+3 sequence (SEQ ID NO:25) was transcribed actively in sterol-deprived cells and was repressed by more than 80% when sterols were present. Binding of SREBP to the SRE-1 sequence, assessed by gel mobility shift assays, correlated precisely on a nucleotide-by-nucleotide basis with the transcriptional activity of each of 18 synthetic promoters with point mutations in Repeat 2 (SEQ ID NO:2 through SEQ ID NO:19, respectively). The SREBP bound to the 9 mutant promoters that were positive for sterol-regulated transcription (SEQ ID NO:2 through SEQ ID NO:4, SEQ ID NO:10, and SEQ ID NO:15 through SEQ ID NO:19, respectively), and it did not bind to any of the 9 point mutants that abolished transcription (SEQ ID NO:5 through SEQ ID NO:9, SEQ ID NO:11, and SEQ ID NO:11 through SEQ ID NO:14, respectively).

A. Materials and Methods

1. Materials. Enzymes used in plasmid constructions were obtained from Pharmacia LKB Biotechnology, Inc. and Life Technologies, Inc.; chromatography supplies and the FPLC system from Pharmacia LKB; Dulbecco's modified Eagle medium, high glucose formulation (DMEM), from JRH Biomedicals, Inc.; sterols from Steraloids, Inc.; protease and phosphatase inhibitors from Sigma Chemical Co. and Boehringer Mannheim; [$^{14}$C]chloramphenicol (55 mCi/mmol) from Amersham; and [$\alpha$-$^{32}$P]dCTP (3000 Ci/mmol) from Dupont-New England Nuclear. Newborn calf lipoprotein-deficient serum (d>1.215 g/ml) was prepared by ultracentrifugation (Goldstein, et al., 1983).

Figures 3A, 3B:
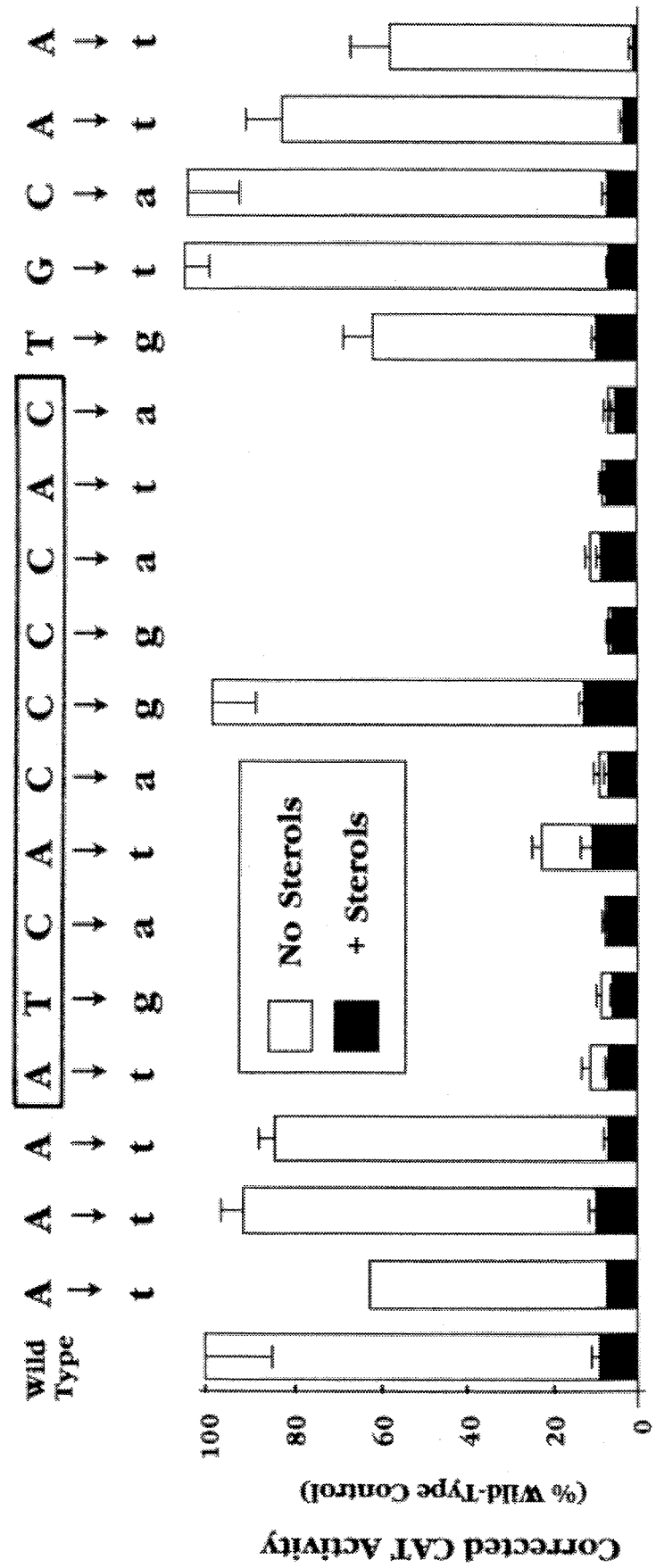
FIG. 3A (Upper panel). Schematic diagram of the data in Table II, which represents the mean ±S.E. of 3 to 9 independent transfection studies. The sequence in upper case letters is designated SEQ ID NO:1. The mutant sequences which each contain the sequence of SEQ ID NO:1 with the exception, in each case, of the single mutation indicated by the lower case letters are designated as SEQ ID NO:2 through SEQ ID NO:19, respectively. The data represent the relative CAT expression observed when cells were cultured in the absence (open bar) or presence (closed bar) of sterols.
FIG. 3B (Lower panel). A single study in which all 19 plasmid constructs were transfected, and the CAT activity of the transfected cells cultured in the absence (−) or presence (+) of sterols was assayed by thin layer chromatography. The chromatogram was exposed for 24 hours at room temperature. The SRE-1 (sequence SEQ ID NO:27) contained within Repeat 2 is boxed.
Figures 4A, 4B:
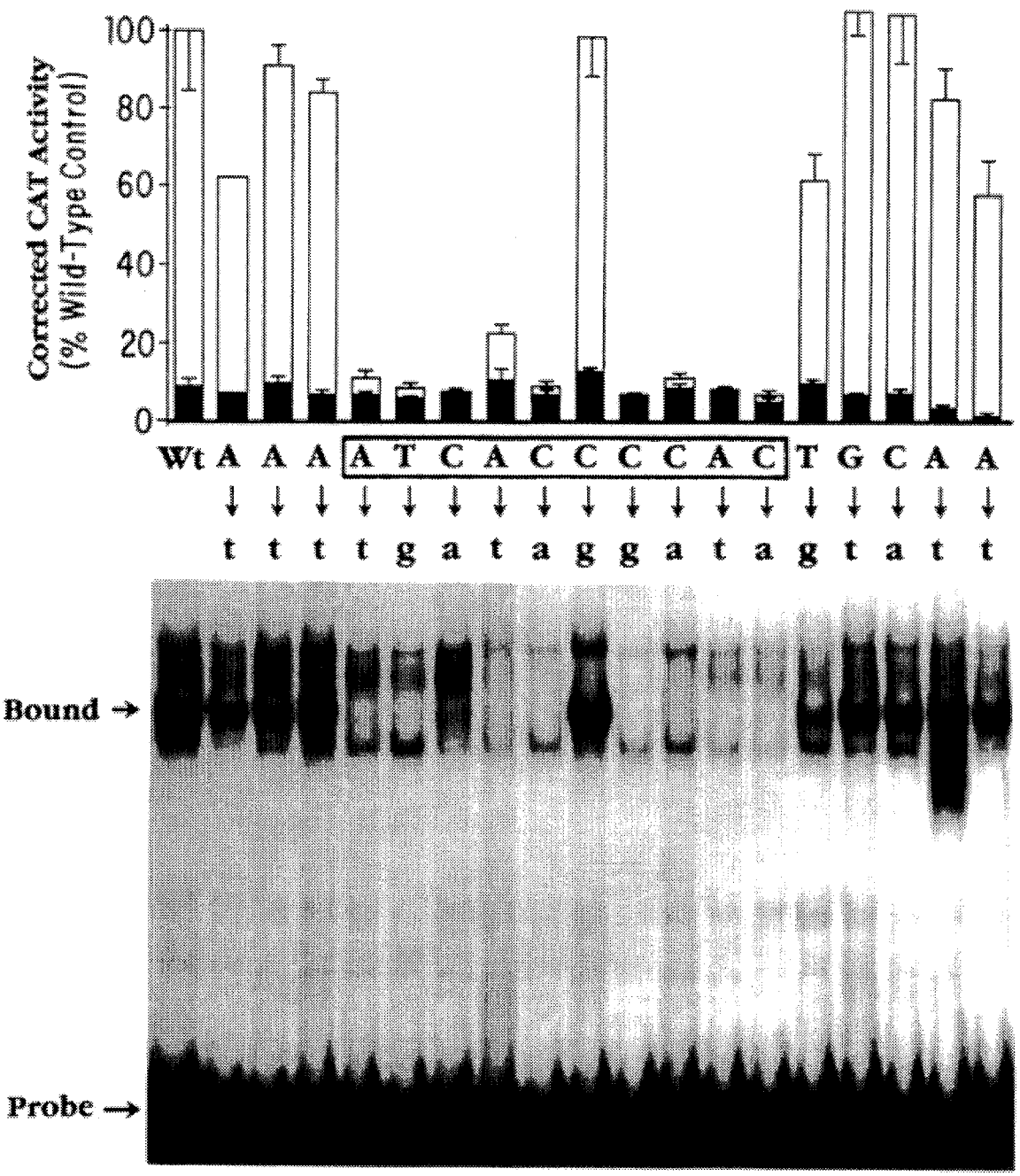
FIG. 4A (Upper panel). Schematic representation of the transfection data in Table II.
FIG. 4B (Lower panel). An aliquot of partially purified rat liver SREBP (2.2 μg) was incubated for 20 minutes at room temperature with the indicated wild-type or mutant $^{32}$P-labeled, PCR-derived DNA probe of 94 bp in length. Each $^{32}$P-probe (∼4×10$^4$ cpm/reaction) contained two tandem copies of Repeat 2+3 with the indicated point mutation in both copies of Repeat 2. After electrophoresis, the gel was exposed to Kodak XAR film for 14 hours at −80° C. with an intensifying screen. The SRE-1 sequence (SEQ ID NO:27) contained within Repeat 2 is boxed.

2. Plasmid Constructions. Plasmid pCMV-$\beta$GAL ($\beta$-galactosidase under control of the human cytomegalovirus promoter) was obtained from Karl Normington (University of Texas Southwestern Medical Center at Dallas). Plasmids were constructed by standard methods (Sambrook et al., 1989) using annealed complementary deoxyoligonucleotides cloned into an E1b TATA-CAT vector (Lillie et al., 1989) digested with either SalI (FIG. 2 and Table I) or PstI-SalI (FIGS. 3 and 4 and Table II). Oligonucleotides were synthesized on an Applied Biosystems 380B DNA synthesizer. Plasmids were purified on Qiagen-tip 2500 columns. DNA sequences of all constructs were determined with a $^{32}$P-labeled SP6 primer using a Sequenase Version 2.0 sequencing kit from United States Biochemicals, Inc. according to the supplier's instructions.

3. DNA Transfection. All cells were grown in an 8% $CO_2$ incubator at 37° C. African green monkey kidney CV-1 cells (obtained from American Type Culture Collection, No. CCL70) were grown in monolayers in medium A (DMEM with 100 U/ml penicillin and 100 µg/ml streptomycin sulfate) containing 10% (v/v) fetal calf serum.

On day 0, the CV-1 cells were plated at $5\times10^5$ cells per 90-mm petri dish and incubated for 24 hours. On day 1, each dish received 10 ml of fresh medium A containing 10% fetal calf serum and were then transfected with calcium phosphate-precipitated DNA (Sambrook et al., 1989). Briefly, 12.5 or 25 µg of test plasmid DNA and 7.5 or 15 µg of pCMV-$\beta$GAL in 0.44 ml of 10 mM Tris-HCl/1 mM EDTA at pH 8.0 were added to 0.11 ml of 2.5 M $CaCl_2$ and mixed with 0.55 ml of 2X Hanks' buffered saline solution (Sambrook et al., 1989). The precipitate was allowed to form for 45 minutes at room temperature, after which 1 ml was added dropwise to each monolayer. The cells were incubated for 14 hours with the DNA, and then washed twice with 6 ml of warm Dulbecco's phosphate-buffered saline, and re-fed with 8 ml of medium A containing 10% calf lipoprotein-deficient serum in the presence or absence of sterols (10 µg/ml cholesterol plus 1 µg/ml 25-hydroxycholesterol added in 16 µl ethanol). After incubation for 48 hours (day 4), the cells were harvested for measurement of CAT and $\beta$-galactosidase activity.

4. CAT Assay. Transfected cells were washed three times with phosphate-buffered saline, scraped into 1 ml of 40 mM Tris-HCl/1 mM EDTA/150 mM NaCl at pH 7.4, lysed by shearing through a 25-gauge needle ten times, and centrifuged at 14,000 g for 2 minutes at 4° C. An aliquot of the supernatant (15–25 µg protein) was incubated for 1–2 hours at 37° C. in a standard CAT assay (Gorman et al., 1982) in a final volume of 0.15 ml containing 0.9 nmol [$^{14}$C]chloramphenicol (50 nCi) and either 0.53 mM acetyl CoA or 0.53 mM butyryl CoA (Pothier et al., 1992). All assays were linear with respect to time of incubation and concentration of extract protein.

The reaction products were quantified by either of two methods. In one method (Table I), the ethyl acetate-solubilized reaction products were chromatographed on Merck 5748 silica gel plates developed in a chloroform/methanol (95/5, v/v) solvent system. The plates were dried and exposed at room temperature to Kodak X-OMAT XAR film for the indicated time. The radioactive spots were cut out and counted in a scintillation counter.

In the second method (Table II), the reaction products were extracted with 0.5 ml xylenes (Seed et al., 1988). The xylene phase was back-washed twice with 0.2 ml of 0.25M Tris-HCl, pH 8, after which a 350-µl aliquot of the xylenes phase was counted in a scintillation counter. The protein content of cell extracts was measured by the Lowry method (Lowry et al., 1951).

5. $\beta$-Galactosidase Assay. An aliquot of the 14,000 g supernatant from the lysed transfected cells (15–25 µg protein) was incubated at 28° C. for 15–60 minutes with 0.67 mg/ml o-nitrophenyl-$\beta$-D-galactopyranoside in a final volume of 1.2 ml (Lee et al., 1984). Reactions were stopped with 0.5 ml 1M $Na_2CO_3$, and the amount of o-nitrophenol formed was measured spectrophotometrically at 420 nm.

6. Partial Purification of Rat Liver SRE-1 Binding Protein (SREBP). An extract of rat liver nuclei was prepared by the method of Lichtsteiner, et al. (Lichtsteiner et al., 1987). Livers from 100 rats rinsed with cold Dulbecco's phosphate-buffered saline (JRH Biosciences) containing protease inhibitors (1 mM benzamidine, 0.5 mM phenylmethylsulfonyl fluoride, 10 µg/ml leupeptin, 5 µg/ml pepstatin, 28 milli-trypsin inhibitory units of aprotinin) and phosphatase inhibitors (1 mM EDTA, 1 mM EGTA, 1 mM $\beta$-glycerophosphate, 5 mM sodium fluoride, 1 mM sodium molybdate) were homogenized at 4° C. for 30 sec in a specially designed Waring blender (circular design with cap to exclude air) (Lichtsteiner et al., 1987) in 4 volumes of Buffer A (10 mM Hepes-KOH, pH 7.6, 2M sucrose, 25 mM potassium chloride, 0.15 mM spermine, 0.5 mM spermidine, 1 mM EDTA, 1 mM DTT, protease inhibitors, and phosphatase inhibitors).

After filtration through 4 layers of cheesecloth, 30 ml of homogenate were layered over 10 ml of Buffer A in AH629 tubes and centrifuged at 103,600 g at 4° C. for 30 minutes. The nuclear pellets were suspended in nuclear lysis buffer (10 mM Hepes-KOH, pH 7.6, 100 mM potassium chloride, 3 mM magnesium chloride, 1 mM DTT, 10% [v/v] glycerol, protease and phosphatase inhibitors) using the B pestle of a Dounce homogenizer and adjusted to a final concentration of 15 $A^{260}$ units/ml. Twenty-eight ml of the nuclear suspension were dispensed into high-speed centrifugation tubes to which 2.8 ml of 4M ammonium sulfate, pH 7.9 (0.36M final concentration) was added and mixed by gentle inversion. The extract was rocked gently for 30 minutes at 0° C. After centrifugation at 244,300 g at 4° C. for 1 h, the supernatant (nuclear extract) was dialyzed against a 100-fold excess of Buffer B (25 mM Hepes-KOH, pH 7.6, 12 mM magnesium chloride, 10% glycerol, 0.5 mM DTT, protease and phosphatase inhibitors) at 4° C. for 2–3 hours. The dialysis was stopped when the conductivity of the nuclear extract became equivalent to that of Buffer B containing 100 mM KCl. Insoluble material was removed by centrifugation at 24,000 g for 15 minutes at 4° C.

The supernatant (425 mg protein) was applied to an S-Sepharose (SP Sepharose, Pharmacia) column (20-ml bed volume) equilibrated with Buffer B containing 100 mM KCl. The column was washed with 2 column volumes of Buffer B containing 100 mM KCl, and the fraction containing the SREBP activity was eluted with Buffer B containing 300 mM KCl. Solid ammonium sulfate was added to the eluate (40 ml), and the pellet obtained at 50% saturation was dissolved in 6 ml and clarified by centrifugation. The resulting solution (88 mg protein in 6 ml) was applied to an FPLC HiLoad™ 16/60 Superdex 200 column equilibrated in Buffer B containing 100 mM KCl. Fractions were assayed for SREBP activity, and the active fractions were pooled and stored at −80° C.

7. PCR Probes for Gel Mobility Shift Assay. Each PCR probe was synthesized in a 100-µl reaction containing 10 mM Tris-HCl, pH 9.0 (at 25° C.), 50 mM KCl, 0.1% [v/v] Triton X-100, 50 µM dGTP, 50 µM dATP, 50 µM dTTP, and 5 µM dCTP, 10 µl [α-$^{32}$P]dCTP (3000 Ci/mmol), 100 ng of the corresponding plasmid used for the transfection studies (see above), and 1 nmol each of two PCR oligonucleotides designed to hybridize to the flanking sequences of the two copies of Repeat 2+3 of the LDL receptor promoter in Plasmid K (5' oligo GACACTATA-GAACTCGAGCAGCTGAAGCTTGCATGC (SEQ ID NO:28); 3' oligo GGTACCCGGGGATCCATTATATACC (SEQ ID NO:29). The reaction was initiated by adding 2 U of Taq DNA Polymerase (Promega), and the tubes were incubated at 94° C. for 30 s, 55° C. for 1.5 min, 72° C. for 1 min, for 15 cycles.

The PCR products were subsequently digested with XbaI and Hind III, and the $^{32}$P-labeled 94-bp double-stranded fragment with a 5' overhang of 4 nucleotides was purified on a 6% polyacrylamide gel. This $^{32}$P-fragment contains two copies of Repeat 2+3 from the LDL receptor promoter region linked by a SalI site (70 bp) surrounded by 16 bp of 5'-flanking sequence (HindIII site) and 7 bp of 3'-flanking sequence (XbaI site).

8. Gel Mobility Shift Assay. The binding activity of SREBP was assayed in a 20-µl reaction containing 12.5 mM Hepes-KOH (pH 7.5), 6 mM $MgCl_2$, 5.5 mM EDTA, 50 mM KCl, 0.5 mM DTT, 0.25 mg/ml non-fat dry milk (Kroger brand), 50 µg/ml sodium polyd(I-C).polyd(I-C) (Pharmacia; average length, 1332 bp), 5% (v/v) glycerol, 25 µg/ml of a double-stranded oligonucleotide containing one copy of a 9-bp scrambled (underlined below) mutant version of Repeat 2 followed by one copy of a wild-type Repeat 3 sequence (5' TCGACAAAAGATAAGATGTG-CAAACTCCTCCCCCTGCG-3', SEQ ID NO:30), 2.2 µg partially purified rat liver SREBP, and 6 fmol of the indicated $^{32}$P-labeled PCR-generated probe (40,000 cpm). Each reaction mixture was incubated at room temperature for 20 minutes and then loaded directly onto a 4% polyacrylamide gel in 0.5X TBE buffer (1X TBE buffer contains 90 mM Tris-borate/2 mM EDTA). The gel was run at constant current of 22 mA at room temperature for 90 minutes and exposed wet to Kodak XAR film overnight at −80° C.

B. Results

Figure 1C:
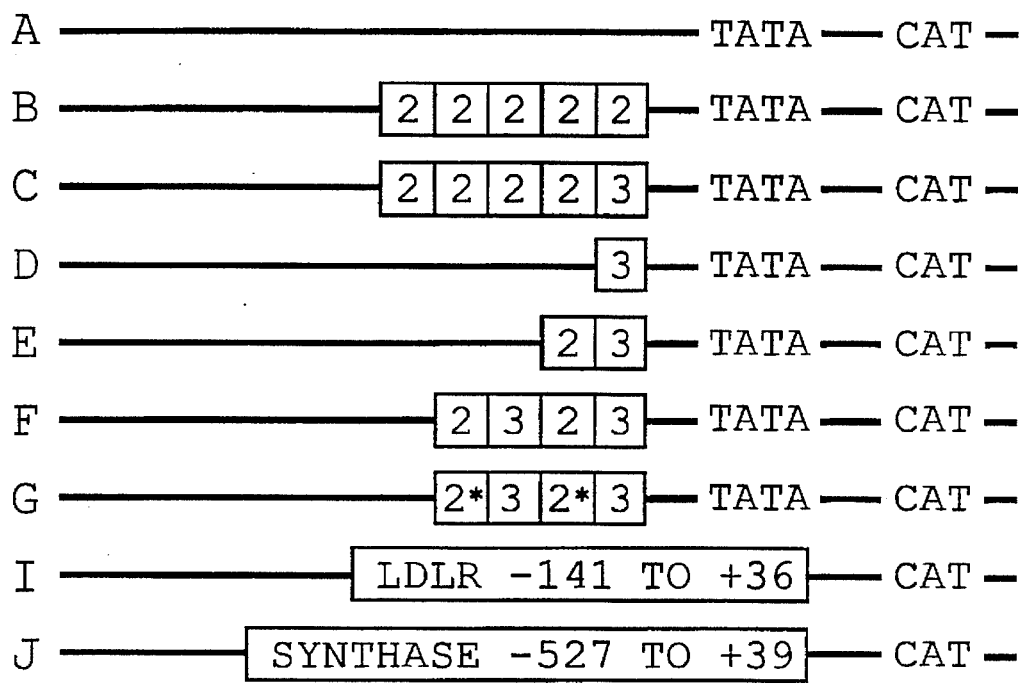
FIG. 1C, plasmids B and C were constructed by inserting annealed complementary oligonucleotides consisting of five contiguous elements with SalI cloning sites at both ends. Plasmids D to G were made by ligating the indicated oligonucleotides in SalI-digested, phosphatase-treated E1b TATA-CAT vector and sequenced to confirm orientation. LDL receptor (LDLR) and HMG CoA synthase constructs refer to plasmids pLDLR-CAT- 234 (Sëdhof et al., 1987) and pSyn-CAT-1 (Smith et al., 1988), described in the indicated references.
Figure 1D:
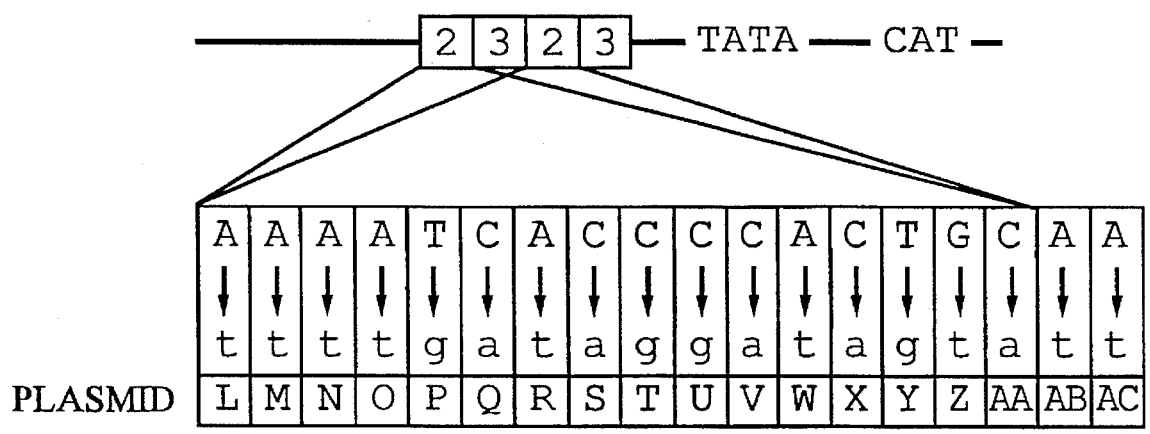
FIG. 1D, the wild-type nucleotide sequence of LDL receptor Repeat 2 plus two adjacent base pairs of Repeat 3 (Plasmid K) is shown in capital letters (SEQ ID NO:1). The corresponding single base changes in mutant plasmids L to Z and AA to AE are shown in lower case letters. These plasmids contain the sequences designated as SEQ ID NO:2 through SEQ ID NO:19, respectively. Each of the 18 plasmids contained two copies of the mutant Repeat 2+3 construct in tandem upstream of the TATA box in the PstI-SalI-digested vector.

FIG. 1 shows the DNA sequences of Repeats 2 (SEQ ID NO:22) and 3 (SEQ ID NO:23), which are immediately contiguous in the native LDL receptor promoter (Sudhof et al., 1987). Plasmid constructs were prepared that contain multiple copies of a Repeat 2+3 oligonucleotide (SEQ ID NO:24) inserted 15 bp upstream of a TATA box sequence derived from the adenovirus E1b promoter. These synthetic promoters were cloned upstream of a reporter gene encoding bacterial chloramphenicol acetyltransferase (CAT) and introduced into monkey CV-1 cells in transient expression assays.

FIG. 2 shows the CAT activity in CV-1 cells that were transiently transfected with the various promoter constructs and incubated for 48 hours either in the absence or presence of sterols. When no LDL receptor promoter elements were present in the vector, no CAT activity was obtained (Plasmid A). Five copies of Repeat 2 (SEQ ID NO:22) also showed no activity (B). A single copy of Repeat 3 (SEQ ID NO:23) gave only low levels of non-regulated transcription (D). However, when the construct contained four copies of Repeat 2 (SEQ ID NO:22) plus a single copy of Repeat 3 (SEQ ID NO:23), transcription was observed in the absence of sterols and was repressed when sterols were present (C). A single copy of the Repeat 2+3 element (SEQ ID NO:24) gave low level transcription that was sterol-regulated (E) similar to that of the native LDL receptor (I). A much higher level of regulated transcription was observed when the Repeat 2+3 element (SEQ ID NO:24) was repeated twice (F). The induced level of transcription of this plasmid was much higher than was seen with the native LDL receptor promoter under the same conditions (I).

In a vector that contained two copies of the Repeat 2+3 sequence (SEQ ID NO:25), a 4-bp mutation in both copies of Repeat 2 reduced transcription to a low level that was similar in the absence and presence of sterols (G), indicating that sterol responsiveness had been abolished. This mutation contains two nucleotide substitutions that were previously shown to obliterate SRE-1 function in the native LDL receptor promoter (Smith et al., 1990).

Table I presents a quantitative analysis of the above expression data. As an internal control for transfection efficiency, in each study a control plasmid was included that encodes β-galactosidase under the direction of the CMV promoter. The observed CAT activity was normalized for the amount of β-galactosidase activity in the same cells, and the results are expressed as corrected CAT activity. The ratio of corrected CAT activities in the absence and presence of sterols is the fold regulation. Table I shows the mean results from 4 to 8 independent studies for each plasmid. In the absence of sterols, the CAT activity in CV-1 cells rose from 5.2 to 62% [$^{14}$C]chloramphenicol conversion when the number of copies of the Repeat 2+3 element (SEQ ID NO:24) was increased from 1 to 2. The dependence of transcription on sterol deprivation also increased from 2.5 to 5.3-fold when the Repeat 2+3 sequence (SEQ ID NO:24) was duplicated. The fold regulation by sterols was highest (14-fold) when four copies of Repeat 2 (SEQ ID NO:22) were placed adjacent to one copy of Repeat 3, SEQ ID NO:23 (Plasmid C).

TABLE I

Sterol-Mediated Regulation of E1b TATA-CAT Genes Containing LDL Receptor Promoter Elements in Transfected CV-1 and HeLa Cells

| Plasmid | Promoter Element | Transfected Cell Type | β-Galactosidase Activity | | Corrected CAT Activity | | Fold Regulation of CAT[§] |
|---|---|---|---|---|---|---|---|
| | | | − Sterols | + Sterols | − Sterols | + Sterols | |
| | | | nmol/min/mg protein | | % conversion | | |
| A | None | CV-1 (n = 4)[‡] | 341 ±11[¶] | 409 ±6.6 | 0.17 ± 0.02[¶] | 0.16 ± 0.01 | 1.1 |
| I | LDL Receptor (−141 to +36) | CV-1 (n = 8) | 118 ± 11 | 193 ± 21 | 6.8 ± 0.9 | 1.9 ± 0.3 | 3.6 |
| J | HMG CoA Synthase (−527 to +39) | CV-1 (n = 6) | 124 ± 13 | 135 ± 21 | 32 ± 6.9 | 6.1 ± 0.6 | 5.2 |
| B | [2]$_5$ | CV-1 (n = 4) | 323 ± 15 | 374 ± 6.4 | 0.42 ± 0.1 | 0.17 ± 0.02 | 2.5 |
| C | [2]$_4$ + 3 | CV-1 (n = 4) | 242 ± 4.7 | 380 ± 3.2 | 15 ± 0.9 | 1.1 ± 0.1 | 14 |
| D | 3 | CV-1 (n = 8) | 273 ± 23 | 324 ± 23 | 0.81 ± 0.14 | 0.88 ± 0.17 | 0 |
| E | 2 + 3 | CV-1 (n = 6) | 223 ± 3.4 | 292 ± 15 | 5.2 ± 0.3 | 2.1 ± 0.1 | 2.5 |
| F | [2 + 3]$_2$ | CV-1 (n = 4) | 277 ± 46 | 298 ± 49 | 62 ± 6.0 | 11.8 ± 2.1 | 5.3 |
| G | [2* + 3]$_2$ | CV-1 (n = 4) | 241 ± 41 | 310 ± 38 | 5.2 ± 0.3 | 5.5 ± 0.4 | 0 |

The indicated cell type was transiently transfected with 25 μg of the E1b TATA-CAT vector containing the indicated LDL receptor promoter element together with 15 μg of pCMV-βGAL. After incubation for 48 hours in the absence or presence of 10 μg/ml cholesterol plus 1 μg/ml 25-hydroxycholesterol, the cells were harvested for duplicate measurement of CAT and β-galactosidase activities as described in the "Materials and Methods". CAT activity in an individual study was corrected for variation in transfection efficiency by normalizing the value to the β-galactosidase activity in the same extract. In each study, the first β-galactosidase value assayed was assigned an arbitrary value of 1 and all other β-galactosidase values were expressed as fractional equivalents of this value. Plasmid J, the authentic HMG CoA synthase promoter fused to CAT, is included for comparative purposes. In the promoter element column, 1 designates SEQ ID NO: 22, 2 designates SEQ ID NO: 23 and 2* + 3 designates SEQ ID NO: 25.
[§]Fold regulation is the ratio of corrected CAT activity in the absence of sterols divided by corrected activity in the presence of sterols.
[‡]Number in parenthesis denotes the number of independent transfection studies.
[¶]Mean ± S.E. of the indicated number of independent transfection studies.

A nucleotide-by-nucleotide mutational analysis of Repeat 2 is shown graphically in FIG. 3, and the data are provided in detail in Table II. For this purpose, construct K was used, which contains two copies of the wild-type Repeat 2+3 (SEQ ID NO:24) element cloned into the E1b CAT vector as a PstI-SalI insert. In this synthetic promoter, the point mutations gave essentially all-or-none results. This allowed the identification of a sequence of 10 nucleotides, SEQ ID NO:27, within Repeat 2, SEQ ID NO:22, of which 9 were essential for high level transcription in the absence of sterols. The only exception was the sixth nucleotide within this sequence, namely, the second C in the CCCC tetramer. Replacement of this C with a G did not affect transcription. This nucleotide is an A in the wild-type hamster Repeat 2 element, SEQ ID NO:20 (Bishop, 1992), which is fully active in transcription (Plasmid AD, Table II). With this sole exception, mutation of any single nucleotide within the SRE-1 severely reduced transcription in the absence of sterols, but did not affect constitutive transcription in the presence of sterols.

TABLE II

Sterol-mediated Regulation of E1b TATA-CAT Genes Containing Single Point Mutations in Repeat 2 of LDL Receptor Promoter in Transfected CV-1 Cells

| Plasmid | Repeat 2 Mutants | | | | | | | | | | | | | | | | | |
|---|---|---|---|---|---|---|---|---|---|---|---|---|---|---|---|---|---|---|
| K | A | A | A | A | T | C | A | C | C | C | C | A | C | T | G | C | A | A |
| L | t | — | — | — | — | — | — | — | — | — | — | — | — | — | — | — | — | — |
| M | — | t | — | — | — | — | — | — | — | — | — | — | — | — | — | — | — | — |
| N | — | — | t | — | — | — | — | — | — | — | — | — | — | — | — | — | — | — |
| O | — | — | — | t | — | — | — | — | — | — | — | — | — | — | — | — | — | — |
| P | — | — | — | — | g | — | — | — | — | — | — | — | — | — | — | — | — | — |
| Q | — | — | — | — | — | a | — | — | — | — | — | — | — | — | — | — | — | — |
| R | — | — | — | — | — | — | t | — | — | — | — | — | — | — | — | — | — | — |
| S | — | — | — | — | — | — | — | a | — | — | — | — | — | — | — | — | — | — |
| T | — | — | — | — | — | — | — | — | g | — | — | — | — | — | — | — | — | — |
| U | — | — | — | — | — | — | — | — | — | g | — | — | — | — | — | — | — | — |
| V | — | — | — | — | — | — | — | — | — | — | a | — | — | — | — | — | — | — |
| W | — | — | — | — | — | — | — | — | — | — | — | t | — | — | — | — | — | — |
| X | — | — | — | — | — | — | — | — | — | — | — | — | a | — | — | — | — | — |
| Y | — | — | — | — | — | — | — | — | — | — | — | — | — | g | — | — | — | — |
| Z | — | — | — | — | — | — | — | — | — | — | — | — | — | — | t | — | — | — |
| AA | — | — | — | — | — | — | — | — | — | — | — | — | — | — | — | a | — | — |
| AB | — | — | — | — | — | — | — | — | — | — | — | — | — | — | — | — | t | — |
| AC | — | — | — | — | — | — | — | — | — | — | — | — | — | — | — | — | — | t |
| AD* | — | — | — | — | — | — | — | a | — | — | — | — | — | — | — | — | — | — |
| AE* | — | — | — | — | — | — | — | — | — | — | — | — | t | — | — | — | — | — |

| Plasmid | Corrected CAT Activity | | | Fold Regulation§ |
|---|---|---|---|---|
| | (−) Sterols | (+) Sterols | | |
| | % of wild-type control | | | |
| K | 100 ± 10.3¶ | 9.1 ± 1.2 | (n = 9)‡ | 11 |
| L | 62 | 7.4 | (n = 1) | 8.4 |
| M | 91 ± 5.6 | 9.7 ± 1.4 | (n = 3) | 9.4 |
| N | 84 ± 3.7 | 6.8 ± 1.1 | (n = 3) | 12 |
| O | 11 ± 2.1 | 6.7 ± 0.7 | (n = 3) | 1.6 |
| P | 8.7 ± 1.3 | 6.1 ± 0.5 | (n = 3) | 1.4 |
| Q | 7.8 ± 0.6 | 6.7 ± 0.6 | (n = 3) | 1.2 |
| R | 22 ± 2.0 | 10 ± 2.4 | (n = 4) | 2.2 |
| S | 9.0 ± 1.1 | 6.7 ± 1.0 | (n = 4) | 1.3 |
| T | 99 ± 9.7 | 13 ± 1.0 | (n = 4) | 7.6 |
| U | 6.9 ± 0.5 | 6.0 ± 0.4 | (n = 3) | 1.2 |
| V | 11 ± 1.1 | 8.6 ± 0.9 | (n = 3) | 1.3 |
| W | 8.0 ± 0.5 | 7.3 ± 0.6 | (n = 3) | 1.1 |
| X | 7.0 ± 1.0 | 5.1 ± 0.9 | (n = 3) | 1.4 |
| Y | 62 ± 6.8 | 9.7 ± 0.8 | (n = 3) | 6.4 |
| Z | 106 ± 5.4 | 6.8 ± 0.3 | (n = 3) | 16 |
| AA | 105 ± 12 | 7.5 ± 0.5 | (n = 3) | 14 |
| AB | 83 ± 7.7 | 3.6 ± 0.2 | (n = 3) | 23 |
| AC | 58 ± 7.4 | 1.4 ± 0.1 | (n = 3) | 41 |
| AD* | 50 | 3.6 | (n = 1) | 14 |
| AE* | 95 ± 7.3 | 6.6 ± 0.2 | (n = 3) | 15 |

CV-1 cells were transiently transfected with 12.5 μg of the indicated plasmid containing 2 copies of the Repeat 2 + 3 sequence, with each copy of Repeat 2 bearing the indicated point mutation, together with 7.5 μg of pCMV-βGAL. After incubation for 48 hours in the absence or presence of 10 μg/ml cholesterol plus 1 μg/ml 25-hydroxycholesterol, the cells were harvested for duplicate measurement of CAT and β-galactosidase activities as described in "Materials and Methods". Corrected CAT activities were calculated as described in the legend to Table I and expressed as "% of the wild-type control" value obtained in the same study.
§Fold regulation is the ratio of corrected CAT activity in the absence of sterols divided by the corrected CAT activity in the presence of sterols.
¶Mean ± S.E. of the indicated number of transfection studies.
‡Number in parentheses indicates the number of independent transfection studies.
*Plasmids AD and AE each contain mutant Repeat 2 sequences that correspond to the wild-type Repeat 2 of the LDL receptor promoter in the hamster (Bishop, 1992) and mouse genes, respectively.
The sequences from plasmids K through AE are designated as SEQ ID NO: 1 through SEQ ID NO: 21, respectively.

The present inventors then proceeded to identify a protein in rat liver nuclear extracts that binds SRE-1 in a fashion that is dependent upon each of the 9 nucleotides that are required for transcriptional activity. In order to obtain a clear result, the rat liver nuclear extract was subjected to ion exchange chromatography on S-Sepharose and gel filtration on Superdex, as described in detail hereinbelow (Example 2). The active fractions from the Superdex column were pooled and tested for specificity of DNA binding, using gel retardation assays.

FIG. 4 shows that the partially purified rat liver nuclear extract fraction contained an activity that retarded the migration of a radiolabeled oligonucleotide that consisted of two tandem copies of the Repeat 2+3 sequence (SEQ ID NO:24). Binding was reduced markedly when any of the 9 essential nucleotides within the SRE-1 were mutated. Mutation of the nucleotide at position 6 did not affect this gel shift activity. Mutation of any of the nucleotides that flanked the SRE-1 did not reduce binding appreciably. These results paralleled completely the results obtained for in vivo transcription, as shown in the top panel of FIG. 4.

C. Discussion

In the present example, artificial promoters were constructed containing multiple copies of the repeated sequences from the LDL receptor promoter for use in transient transfection assays to determine precisely the nucleotides that are required for high level sterol-sensitive transcription. The results indicate that a segment of 10 nucleotides within the 16-bp Repeat 2 element, SEQ ID NO:22, contains the sterol-sensitive transcription activity. Mutation of any one of 9 nucleotides within this sequence markedly reduced transcriptional activity of the SRE-1. The sole exception was the nucleotide at position 6 (the second C in the CCCC tetramer).

Repeat 2, SEQ ID NO:22, did not have any detectable transcriptional activity on its own, even when present in five copies. However, when one of these copies was replaced by a single copy of Repeat 3, SEQ ID NO:23, significant sterol-sensitive transcription appeared. A single copy of Repeat 3, SEQ ID NO:23, on its own had virtually no transcriptional activity, either in the absence or presence of sterols. These data are consistent with previous data showing that Repeat 2 synergizes with Repeat 3 in promoting transcription, but only in the absence of sterols (Smith et al., 1990; Sudhof et al., 1987; Dawson et al., 1988).

In the native LDL receptor promoter, Repeats 2 and 3 are immediately adjacent to each other. When constructs were prepared that contained two copies of Repeat 2+3, SEQ ID NO:24, in tandem, sterol-sensitive transcription increased as the number of the Repeat 2 and 3 element units increased. In the mutagenesis studies, the construct that contained two copies of the Repeat 2+3 sequence was used which allowed the demonstration that sterol-dependent transcription in vivo requires every nucleotide in the 10-bp SRE-1 with the exception of one cytosine. Using gel retardation assays, an activity in rat liver nuclear extracts was identified that bound to the SRE-1 sequence in a fashion that was dependent on each of the 9 nucleotides that were required for transcription. Strikingly, the binding of this protein did not depend on the nucleotide in the 6th position, i.e., the second C in the CCCC tetramer. This was also the only nucleotide whose replacement could be tolerated without loss of transcriptional activity. The precision of this correlation makes it highly likely that the DNA binding activity in the rat nuclear extracts is the one that is required for sterol-sensitive transcription.

The goal of this example was to generate a series of probes with single point mutations in the SRE-1 sequence that abolished sterol-regulated transcription and could be used to detect physiologically relevant nuclear binding proteins. The present inventors were not attempting to detect all possible nucleotides that might substitute for the native ones without loss of function. The results of these mutagenesis studies are completely consistent with previous studies in which point mutations were made in the native LDL receptor promoter (Smith et al., 1990). The earlier studies used CHO cells that were permanently transfected with recombinant plasmids containing the native LDL receptor promoter. Those studies delineated the same 10-bp sequence that was identified in this study. They also showed that a transversion at position 6 (C to A mutation) preserved transcriptional activity. However, the fold changes in transcription in the absence and presence of sterols were lower in the earlier study, and several mutations produced intermediate effects. These problems were avoided in the current study through the use of a synthetic construct containing two copies of the Repeat 2+3 unit, SEQ ID NO:24, and through the use of transient transfection assays that gave a larger amplitude of regulation and all-or-none effects of the mutations.

It was necessary to perform the detailed analysis of nucleotide requirements for transcriptional activity described in this Example because of the previous difficulty encountered in identifying a DNA binding protein that correlated with SRE-1-dependent transcription. Nuclear extracts contain many abundant DNA binding proteins that shift the electrophoretic mobility of oligonucleotides that contain the SRE-1 sequence (Rajavashisth et al., 1989; Stark et al., 1992). However, these proteins do not show the specificity of binding that is defined here for a true transcriptional regulator. Once the precise nucleotides were identified, it became possible to exclude other Repeat 2 binding proteins and to focus on the activity that is shown in FIG. 4.

EXAMPLE 2

The Purification of SREBP to Homogeneity from the Nuclei of Human HeLa Cells

The present example describes the purification of SREBP to apparent homogeneity from the nuclei of human HeLa cells.

A. Materials and Methods

1. Materials. SP-Sepharose, CNBr-activated Sepharose 4B, pre-packed Superdex 200 26/60 gel filtration column, and the nucleotides used for PCR were obtained from Pharmacia LKB Biotechnology, Inc; molecular weight markers and Silver Stain Plus Kit were from Bio-Rad; Nonidet P-40 from Pierce Chemical Co.; 5'-bromo-dUTP and Joklik minimum essential medium from Sigma Chemical Co; DNaseI (DPFF grade) from Worthington Biochemical Corp.; micrococcal nuclease from Boehringer Mannheim; and purified human Sp1 from Promega. Other materials were obtained from sources described in Example 1.

2. Cell Culture. Human HeLa S3 cells (obtained from B. Johnson and R. Tjian, University of California, Berkeley, Calif.) were grown in spinner culture at a density of ~2.5–5×10$^5$ cells/ml in 4-liter spinner flasks in Joklik minimum essential medium containing 5% (v/v) newborn calf serum, 100 u/ml penicillin, and 100 µg/ml streptomycin sulfate. The cells were split into an equal volume of fresh complete medium every 24 hours. On the day prior to harvest, the cells were split into an equal volume of medium without serum so that the final concentration of newborn calf serum was 2.5%. Of the total HeLa cells used in the current studies, one half were purchased from the National Cell Culture Center (Minneapolis, Minn.), and the other half were grown in the present inventors' laboratory. HeLa cells obtained from the National Cell Culture Center were shipped overnight as a packed pellet on wet ice and processed within 1 hour of arrival. Pilot studies showed that the SREBP activity in these cells was similar to that in HeLa cells grown in the present inventors' laboratory.

3. Preparation of DNA Affinity Columns. DNA affinity columns were prepared using established methods (Briggs et al., 1986; Kadonaga and Tjian, 1986) in which multimerized double-stranded oligonucleotides were coupled to CNBr-activated Sepharose 4B. Column A contains a multimerized oligonucleotide, each monomer consisting of one copy of a mutant Repeat 2 with a scrambled SRE-1 sequence (underlined below) followed by one copy of a wild-type Repeat 3 (Südhof et al., 1987). Each Repeat 2+3 element is flanked by a 4-bp linker (TCGA). The two sequences that comprise column A are designated SEQ ID NO:31 and SEQ ID NO:32, respectively. Column B contains a multimerized oligonucleotide flanked by a TCGA linker. Each monomer consists of two tandem copies of a wild-type Repeat 2 sequence except for a single bp change (C→T) in the 3' region flanking the SRE-1 sequence (underlined below). This bp change was designed to eliminate a contaminating protein that bound to the flanking sequence. The two sequences that comprise column B are designated SEQ ID NO:33 and SEQ ID NO:34, respectively. Column C contains a multimerized oligonucleotide, each monomer consisting only of the 10-bp SRE-1 sequence flanked by a 4-bp linker (CTAG). The sequences that comprise column C are designated SEQ ID NO:35 and SEQ ID NO:36, respectively. The three double-stranded oligonucleotides used for multimerization have the following sequences (represented by SEQ ID NO:31 through SEQ ID NO:36, respectively):

(330-ml bed volume) using a Fast Protein Liquid Chromatography system (FPLC, Pharmacia Biotechnology, Inc.). The column was equilibrated and eluted in Buffer B containing 0.15M KCl. After 90 ml elution, individual fractions of 4 ml were collected. SREBP activity was typically found in fractions 9–13, which were pooled, frozen in liquid nitrogen, and stored at −80° C. for 1–7 days.

Steps 5 and 6: First DNA Affinity Chromatography—The active fractions from 12 separate Superdex preparations (representing 6 different nuclear extract preparations) were thawed and pooled (498 mg protein in 240 ml), after which sodium EDTA (5 mM) and sodium molybdate (10 mM) were added to achieve the indicated final concentration. The mixture was loaded onto a 20-ml DNA affinity column that contained a mutant version of Repeat 2+a wild-type Repeat 3 (Column A, SEQ ID NO:31 and SEQ ID NO:32, see above). The flow-through containing SREBP activity was collected, and sodium poly(dI-dC).poly(dI-dC) (Pharmacia; average length, 1332 bp) was added to achieve a final concentration of 40 µg/ml. After incubation on ice for 10 min, the mixture was divided into six aliquots, each of which was loaded onto a 1-ml DNA affinity column that contained tandem copies of Repeat 2 (Column B, SEQ ID NO:33 and

| Column A | 5'-TCGACAAAAgataagatatGCAAACTCCTCCCCCTGCG-3' | (31) |
|---|---|---|
| | 3'-GTTTTctattctataCGTTTGAGGAGGGGGACGCAGCT-5' | (32) |
| Column B | 5'-TCGACAAAATCACCCCACTGTAAAATCACCCCACTGTG-3' | (33) |
| | 3'-GTTTTAGTGGGGTGACATTTTAGTGGGGTGACACAGCT-5' | (34) |
| Column C | 5'-GATCATCACCCCACTG-3' | (35) |
| | 3'-TAGTGGGGTGACCTAG-5' | (36) |

4. Purification of the SRE-1 Binding Protein (SREBP). A typical purification is described. All steps were carried out at 4° C.

Step 1: Nuclear Extracts—Nuclear extracts from 75–100 liters of HeLa S3 cells (4–5×10¹⁰ cells) were prepared according to Dignam, et al. (1983) with two modifications. Firstly, the nuclei were extracted with Buffer A (20 mM Hepes-KOH, pH 7.6, 25% (v/v) glycerol, 0.5M NaCl, 1.5 mM MgCl₂, 1 mM sodium EDTA, 1 mM sodium EGTA, and 0.5 mM DTT) supplemented with protease and phosphatase inhibitors (0.5 mM phenylmethylsulfonyl fluoride, 5 µg/ml pepstatin A, 10 µg/ml leupeptin, 2 µg/ml aprotinin, 1 mM sodium β-glycerolphosphate, 5 mM sodium fluoride, and 1 mM sodium molybdate). Secondly, after extraction in Buffer A, the nuclear extract was centrifuged at 24,000 rpm for 3 hours in an AH 629 rotor (Du Pont Sorvall), and the 1.03×10⁵ g supernatant was used for further purification.

Step 2: SP-Sepharose Chromatography—The 1.03×10⁵ g supernatant (1 g protein) was diluted with 3 volumes of Buffer B (25 mM Hepes-KOH, pH 7.5, 12 mM MgCl₂, 10% glycerol, 1 mM sodium EDTA, 1 mM sodium EGTA, 0.5 mM DTT) supplemented with protease and phosphatase inhibitors (see above) and applied onto an SP-Sepharose column (100-ml bed volume) equilibrated with Buffer B containing 0.1M KCl. The column was washed with 2.5 volumes of Buffer B with 0.1M KCl and eluted with 2 volumes of Buffer B with 0.3M KCl.

Steps 3 and 4: Ammonium Sulfate Fractionation and Gel Filtration Chromatography—Solid ammonium sulfate was added to the SP-Sepharose 0.3M KCl eluate (480 mg protein) to achieve 40% saturation, and the mixture was rotated for 3 hours. The ammonium sulfate precipitate was centrifuged (32,600× g for 15 minutes), resuspended in 25 ml Buffer B, and divided into two aliquots. Each aliquot was loaded onto a Superdex 200 26/60 gel filtration column SEQ ID NO:34). The columns were each washed with 30 column volumes of Buffer B containing 0.3M KCl and 0.1% (v/v) Nonidet P-40 (NP-40) and eluted with Buffer B with 1M KCl plus 0.1% NP-40.

Steps 7 and 8: Repeat DNA Affinity Chromatography—The active fractions from the Step 6 eluate (1.7 mg protein in 18 ml) were pooled and dialyzed overnight against Buffer B containing 0.15M KCl and 0.1% NP-40. After dialysis, sodium EDTA and sodium molybdate were added to achieve final concentrations of 5 mM and 10 mM, respectively. The protein was then loaded onto two sequential 2-ml DNA affinity columns containing a mutant version of Repeat 2+a wild-type Repeat 3 (Column A, SEQ ID NO:31 and SEQ ID NO:32). The flow-through fractions were collected and poly(dI-dC).poly(dI-dC) was added to a final concentration of 40 µg/ml. After incubation on ice for 10 min, the mixture was loaded onto a 1-ml DNA affinity column that contained only the SRE-1 portion of Repeat 2 (Column C, SEQ ID NO:35 and SEQ ID NO:36). The column was washed with 30 column volumes of Buffer B containing 0.3M KCl and 0.1% NP-40 and eluted stepwise with 1 ml aliquots of Buffer B containing 0.1% NP-40 and concentrations of NaCl that increased from 0.4M to 1.0M in increments of 0.1M.

Step 9: Glycerol Gradient Sedimentation—The active fractions from Step 8 (0.5M–0.7M NaCl step elutions) were pooled, and a 0.2-ml aliquot of the 3-ml pooled fraction was loaded onto a 4.5 ml 10%–30% (v/v) glycerol gradient containing 25 mM Hepes, 12 mM MgCl₂, 5 mM sodium EDTA, 0.6M NaCl, 1 mM DTT, and 0.1% NP-40 at pH 7.5. The gradient was centrifuged in a SW-60 rotor (Beckman) at 55,000 rpm for 15 hours. Fractions of 0.45 ml were collected from the top.

5. Gel Mobility Shift Assay. PCR probes containing copies of wild-type and mutant Repeat 2+3 elements (SEQ ID NO:28 and SEQ ID NO:29) were prepared and used for gel mobility shift assays as described in Example 1. Unless otherwise stated, gels were exposed to Kodak XAR film at −80° C. for the indicated time with intensifying screens. SREBP activity was quantified by scanning the gel for 15 minutes on the Ambis 100 Radioanalytic Imaging System. Each unit of activity corresponds to 1000 cpm of shifted probe.

6. UV Crosslinking. The general protocol described by Chodosh, et al. (1986) was followed. The $^{32}$P-labeled probes used for UV crosslinking were prepared in the same way as those used for the gel mobility shift assay except that 5'-bromo-dUTP was substituted for dTTP in the PCR reaction. The DNA binding reactions were performed in a 1.5-ml Eppendorf tube in a final volume of 0.1 ml containing 60 fmol $^{32}$P-labeled probe ($5\times10^5$ cpm), ~4 µg of partially purified SREBP (1M KCl eluate from Step 6 that had been dialyzed against Buffer B containing 0.15M KCl and 0.1% NP-40), and the same buffer components used in the gel mobility shift assay. The probes were prepared just prior to the reactions.

After incubation for 20 minutes at room temperature, the Ependorf tubes were placed on ice and exposed to a UV lamp (254 nM) for 1 h, after which a 10-µl aliquot was removed for a gel mobility shift assay. In the remaining 90 µl, the concentration of $MgCl_2$ was adjusted to 10 mM, $CaCl_2$ was added to 10 mM, DNaseI was added to 736 units/ml, and micrococcal nuclease was added to 28 units/ml. Each mixture was incubated at 37° C. for 25 minutes. After nuclease digestion, the samples were precipitated with 10% (w/v) trichloroacetic acid, washed with cold acetone, resuspended in SDS-PAGE sample buffer (Laemmli, 1970), loaded onto an 8% SDS polyacrylamide minigel, and run together with molecular weight markers and purified SREBP. The gel was stained with silver, dried, and exposed to X-ray film.

7. DNase I Footprinting. DNase I footprinting was carried out as described by Briggs et al. (1986) with the following modifications. DNA binding reactions contained, in a final volume of 50 µl, 2 fmol of a single-stranded $^{32}$P-end-labeled DNA fragment (~$10^4$ cpm/tube), 12.5 mM Hepes-KOH (pH 7.5), 6 mM $MgCl_2$, 5 mM sodium EDTA, 50 mM KCl, 0.25 mg/ml nonfat dry milk (Kroger brand), 20 µg/ml poly d(I-C).poly d(I-C), 10% glycerol, 0.5 mM DTT, and the indicated protein fractions. Single 5' end-labeled, double-stranded DNA footprint probes (239 bp) encompassing Repeat 2+3 from Plasmids K and X (SEQ ID NO:24, Example 1) were prepared by sequential digestion with EcoRI, treatment with calf intestinal alkaline phosphatase and T4 polynucleotide kinase in the presence of [$\gamma$-$^{32}$P]ATP, digestion with NdeI, and gel purification.

8. Other Methods. SDS-polyacrylamide gel electrophoresis was carried out as described by Laemmli (1970). The gels were calibrated with high range SDS-polyacrylamide gel electrophoresis standards (Bio-Rad). All protein gels were stained with a Silver Stain Plus Kit from Bio-Rad. Gel filtration columns were calibrated with gel filtration standard markers from Bio-Rad. The protein content of all samples (except Step 8) was determined by the Lowry method (1951). The protein content of purified SREBP in Step 8 was estimated by silver staining and densitometric scanning of an 8% SDS polyacrylamide gel in which known amounts (10 ng to 1 µg) of the bovine serum albumin component of a Bio-Rad standard protein mixture were used as a reference.

B. Results

Although SREBP activity could be visualized with gel mobility shift assays in partially purified extracts of rat liver nuclei, the protein lost activity during purification, and it was not possible to isolate it from this source (Example 1). Similar difficulties were encountered with nuclei from livers of hamsters, rabbits, and cows. On the other hand, the protein from human HeLa cell nuclei was stable and was isolated from large-scale cultures of these cells.

Figures 5A, 5B:
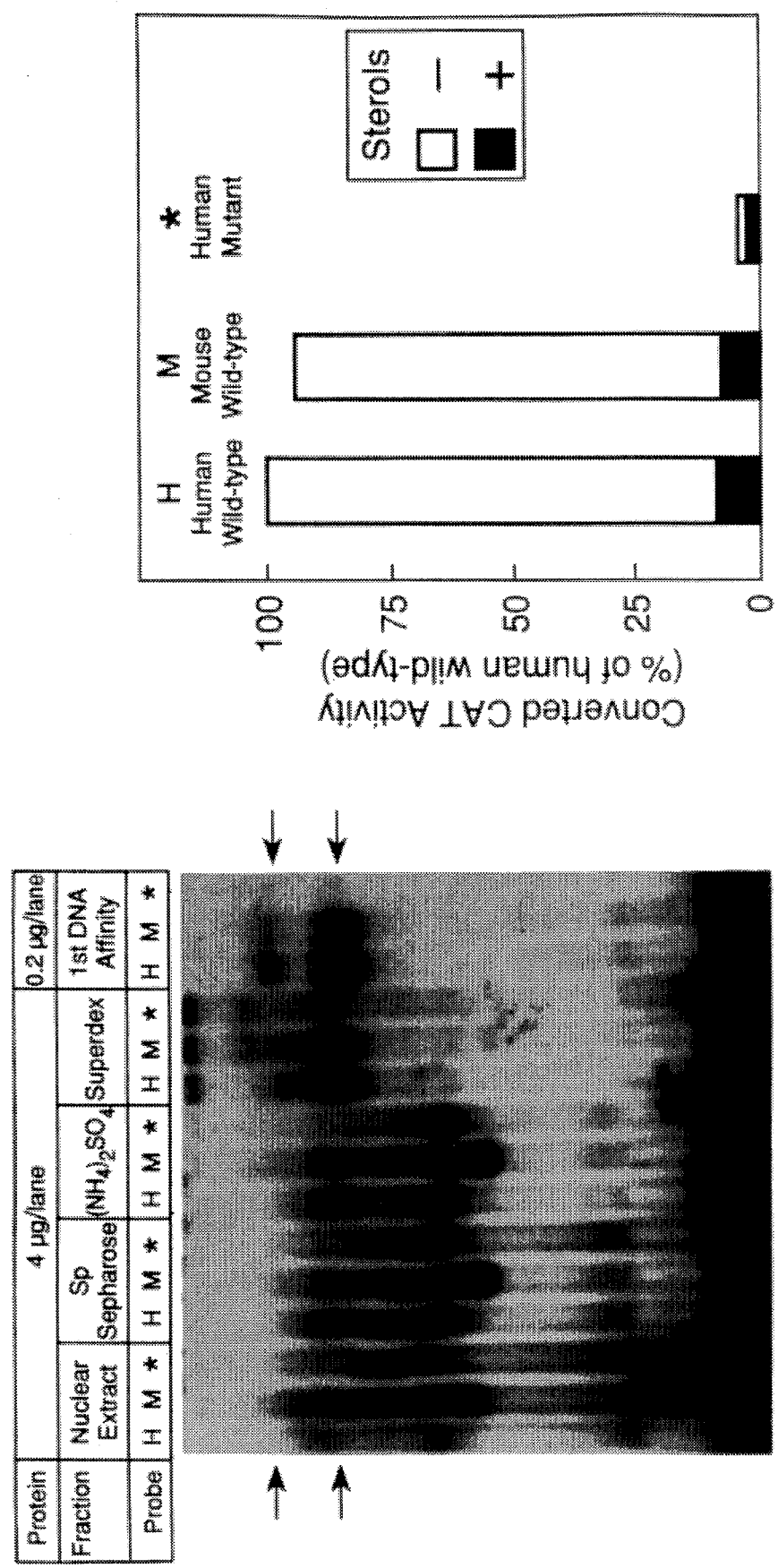
FIG. 5A (Left Panel). Aliquots of the indicated fractions at different stages of purification were incubated in the standard gel shift assay for 20 minutes at room temperature with the indicated $^{32}$P-labeled, PCR-derived DNA probe of 94 bp in length. Each probe (∼4×10$^4$ cpm/reaction) contained two tandem copies of version of Repeats 2+3. The probes contained the following versions of Repeat 2: probe H, wild-type human SRE-1 sequence (Plasmid K in Example 1) (SEQ ID NO:1); Probe M, wild-type mouse SRE-1 sequence (SEQ ID NO:21) which differs by one bp (C→T) from the human sequence (Plasmid AE in Example 1); and Probe *, mutant version of human SRE-1 sequence that contains a substitution of A for C at the same position (SEQ ID NO:14), which abolishes the transcriptional activity of SRE-1 (Plasmid X in Example 1). Arrows denote the position of migration of SREBP bound to one (bottom arrow) or two (top arrow) copies of SRE-1 in the $^{32}$P-probe. The gel was exposed for 2 hours. The 1st DNA affinity fraction had been subjected to sequential purification on DNA affinity Columns A and B.
FIG. 5B (Right Panel), HeLa cells growing in spinner culture were plated onto monolayers at 5×10$^5$ cells per 90-mM dish in medium A (Example 1) containing 10% fetal calf serum. After 24 hours, the cells were transiently transfected with the indicated LDL receptor promoter-CAT plasmid, incubated in the absence or presence of sterols, and processed for measurement of CAT activity as described in Example 1. The data represent the average of two independent transfection studies and are consistent with expression data in simian CV-1 cells (Table II). H, M, and * refer to Plasmids K, AE, and X, respectively.

FIG. 5 shows the results of gel mobility shift assays of SREBP in extracts of HeLa cell nuclei that were subjected to sequential fractionation procedures. As a routine test for specificity during the purification, we used a panel of three $^{32}$P-labelled probes. Probe H consists of two tandem copies of the human Repeat 2+3 sequence, SEQ ID NO:24, and it produces regulated transcription when transfected into HeLa cells (FIG. 5, right panel). Probes M and * also consist of two tandem copies of the Repeat 2+3 sequence, but they differ from the human sequence at one position within the SRE-1 (the most 3' C) in both copies of Repeat 2, SEQ ID NO:14 and SEQ ID NO:21. Probe M contains a T at this position, which corresponds to the wild-type mouse LDL receptor Repeat 2 sequence and is transcriptionally active in HeLa cells (FIG. 5) and in cultured simian CV-1 cells (Example 1). In Probe *, the same 3' C is replaced by an A in both copies of Repeat 2. This mutation inactivates the function of Repeat 2 in HeLa cells (FIG. 5) and in CV-1 cells (Example 1).

In crude nuclear extracts, gel mobility shift assays failed to reveal a shifted band that appeared with Probes H and M, but not *, which was the criterion for specificity (FIG. 5, left panel). Similarly, no such activity was found in a fraction from an SP-Sepharose anion exchange column that was subsequently shown to contain SREBP activity (FIG. 5). However, when this fraction was precipitated with 40% ammonium sulfate, a trace of specific binding activity was observed, i.e., there were two shifted bands (designated by arrows in FIG. 5) that were slightly more intense with the wild-type probes (H and M) than they were with the mutant probe *. A similar hint of specificity was observed in certain column fractions when the ammonium sulfate precipitate was subjected to Superdex gel filtration chromatography (FIG. 6). The active fractions from the Superdex column were then subjected to sequential DNA affinity chromatography on two columns. The first column contained multimerized copies of an oligonucleotide composed of a mutated, transcriptionally inactive form of Repeat 2 adjacent to wild-type Repeat 3. The flow-through fraction from this column was then adsorbed to a column containing multiple tandem copies of Repeat 2 and eluted with buffer containing 1M KCl. The eluate contained an activity that bound strongly to the H and M probes, but did not bind detectably to the mutant probe * (last 3 lanes of left panel of FIG. 5).

FIG. 6 shows assays of SREBP as it emerged from the Superdex gel filtration column, which was the first step at which the specific binding activity could be visualized clearly. The peak fraction (number 11) was between the 670-kDa and 158-kDa markers at a position corresponding to approximately 500 kDa.

Figure 7B:
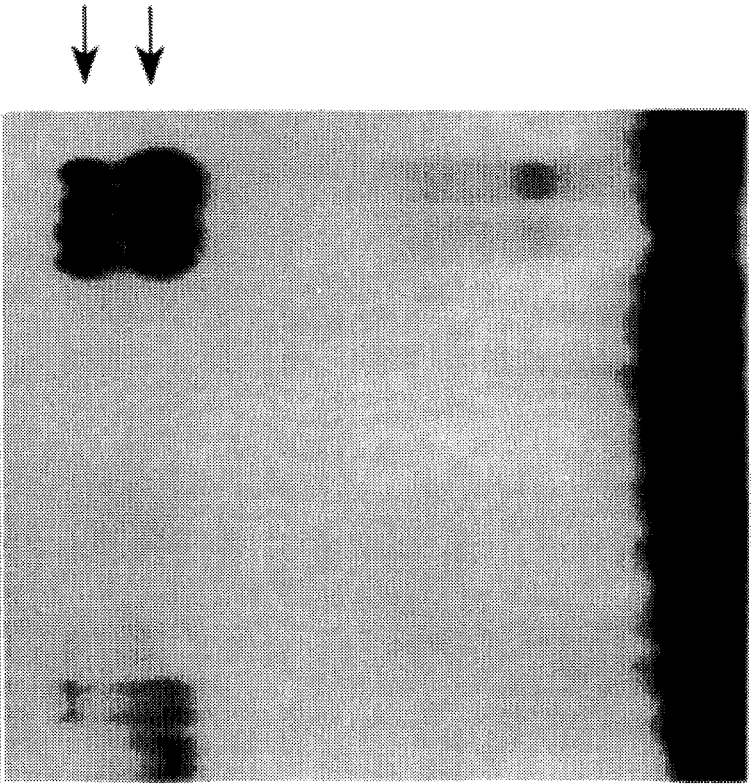
FIG. 7B. The flow-through from Column A was applied directly to Column B containing tandem copies of wild-type Repeat 2 (SEQ ID NO:33 and SEQ ID NO:34) and eluted as described hereinbelow. Aliquots (2 μl) of the starting material, flow-through fraction, 0.3M KCl eluate, and 1M KCl eluate from both columns were assayed for SREBP activity by the standard gel shift assay using the three $^{32}$P-probes described in FIG. 5. The gels were exposed for 2 hours.
Figure 7A:
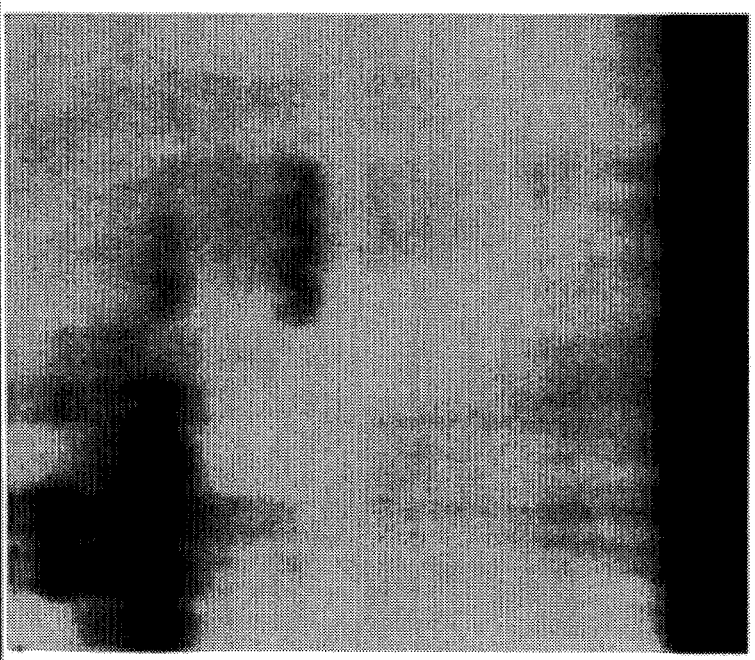
FIG. 7A. Active fractions from the Superdex 200 column (Step 4) were pooled and applied to a DNA affinity column containing a mutant version of Repeat 2+wild-type Repeat 3 (Column A) (SEQ ID NO:31 and SEQ ID NO:32) and eluted as described hereinbelow.

FIG. 7 shows the results of the DNA affinity chromatography steps. The starting material, which was derived from the Superdex column, contained the specific SREBP activity as well as a contaminating protein that bound the mutant * probe. The specific SREBP activity emerged in the flow-through of the first column, which contained an inactive mutant form of Repeat 2 in tandem with wild-type Repeat 3 (SEQ ID NO:31 and SEQ ID NO:32) (FIG. 7A). When this flow-through material was applied to a column containing oligomerized Repeat 2, the binding activity was adsorbed, Step 4 as the starting point.

TABLE III

Purification of SREBP from Human HeLa Cells

| Step | Fraction | Protein* mg | Specific Activity† units/mg | Total Activity units | Purification -fold | Recovery % |
|---|---|---|---|---|---|---|
| 1 | Nuclear Extract | 6009 | — | — | — | — |
| 2 | SP-Sepharose | 2900 | — | — | — | — |
| 3 | Ammonium Sulfate | 1382 | — | — | — | — |
| 4 | Superdex 200 | 498 | 230 | 114,540 | 1 | 100 |
| 5 | Mutant Repeat 2 DNA Affinity (Column A) | 445 | 212 | 94,340 | 0.82 | 82 |
| 6 | Specific DNA Affinity (Column B) | 1.7 | 50,405 | 85,688 | 219 | 75 |
| 7 | Mutant Repeat 2 DNA Affinity (Column A) | 0.97 | 70,230 | 68,123 | 305 | 59 |
| 8 | Specific DNA Affinity (Column C) | 0.004 | 8,784,000 | 35,136 | 38,191 | 31 |

Nuclear extracts were prepared from a total of ~500 liters of HeLa cells spinner culture (representing 6 different preparations) as described in the "Materials and Methods". SREBP activity of fractions was assayed by the standard gel mobility shift assay at two concentrations of protein. Activity could not be accurately measured in fractions derived from Steps 1–3.
Column A contains SEQ ID NO: 31 and SEQ ID NO: 32; Column B contains SEQ ID NO: 33 and SEQ ID NO: 34; and Column C contains SEQ ID NO: 35 and SEQ ID NO: 36.
*Protein concentration of the various fractions was determined as described in "Materials and Methods".
†One unit of activity is defined as described in "Materials and Methods".

and it did not appear in the 0.3M KCl eluate (SEQ ID NO:33 and SEQ ID NO:34) (FIG. 7B). It was eluted when the concentration of KCl was raised to 1.0M. This 1.0M KCl eluate was free of the contaminating material that bound the mutant * probe. The arrows in FIG. 7B represent shifted bands containing the SREBP bound to one or both copies, respectively, of the Repeat 2 sequence in the probe.

To complete the purification of the SREBP, the 1.0M KCl eluate from the Repeat 2+3 column was applied to another column containing oligomers of the 10-bp SRE-1 flanked only by a 4-bp linker whose nucleotides differed from the flanking nucleotides in Repeat 2 (SEQ ID NO:35 and SEQ ID NO:36). This column was eluted stepwise with aliquots of solutions containing 0.1M increments of NaCl from 0.4M to 1.0M. Mobility shift assays showed that the peak of SREBP activity was in fraction 6 (0.6M NaCl) with smaller amounts in the adjacent fractions. All of these fractions were subjected to SDS polyacrylamide gel electrophoresis and silver staining. A cluster of protein bands with molecular masses between 59 and 68 kDa co-eluted with the SREBP activity, peaking in fraction 6 (right panel of FIG. 8).

Table III shows quantitative estimates of the results of a complete purification starting with nuclear extract from ~500 liters of HeLa cells, which contained 6 g protein. As shown in FIG. 5, the SREBP activity from early fractions could not be estimated, owing to the presence of contaminating proteins that bound the mutant as well as the wild-type probe on gel mobility shift assays. After the gel filtration chromatography on Superdex 200 (Step 4), approximately 500 mg of protein were recovered, which contained approximately 114,000 units of SREBP activity. Each unit is defined as the activity that shifts 1000 cpm of the specific probe under the standard conditions of the assay. After the four DNA affinity column steps, the amount of protein was reduced by a factor of more than 100,000 (to 4 µg) with a 31% recovery of SREBP activity. The total calculated purification was approximately 38,000-fold with A series of studies were next performed to confirm that the protein bands seen in the purified preparation actually constitute SREBP. In one such study, the purified proteins were subjected to ultracentrifugation on a glycerol gradient, and fractions were assayed for SREBP activity (FIG. 9, left) and for protein content by SDS polyacrylamide gel electrophoresis (FIG. 9, right). The peak of SREBP activity was found in fraction 3, which also contained the cluster of proteins between 59 and 68 kDa. This position of sedimentation corresponded to a molecular mass somewhat less than that of the ovalbumin standard (44 kDa), the peak of which was found in fraction 4.

To further validate the inventors' hypothesis, a partially purified preparation of SREBP was incubated with a $^{32}$P-labeled SRE-1 sequence in which deoxythymidine was replaced with 5-bromodeoxyuridine. After exposure to ultraviolet light and digestion with nucleases, the proteins were subjected to SDS polyacrylamide gel electrophoresis. A cluster of radiolabeled bands was seen in the region of 59 to 68 kDa (FIG. 10, lane 3), which corresponded precisely with the migration of purified SREBP in the same electrophoresis system (lane 6). Labeling was also seen with the M probe (lane 5), but not with the mutant * probe (lane 4). These results suggest that each of the proteins in the 59 to 68 kDa cluster recognizes the SRE-1 element in a specific fashion.

To confirm the specificity of the SREBP for its DNA recognition site, the purified SREBP was subjected to gel mobility shift assays with a panel of 16 mutant probes that were characterized for transcriptional activity in Example 1 (FIG. 11). The SREBP bound only to the probes that were active in transcription, including the probe that contained a G in place of a C at position 6 of the SRE-1. This result confirms that the purified SREBP has a binding specificity that matches exactly with the transcriptional activity of the SRE-1 element (Example 1).

DNaseI footprinting analysis showed that SREBP bound to the SRE-1 sequence within Repeat 2, SEQ ID NO:27, whereas Sp1 bound to Repeat 3, SEQ ID NO:23 (FIG. 12, lanes 1 and 2). The two footprint regions overlapped, with the Sp1 footprint extending partially into Repeat 2. When the SRE-1 sequence was mutated, the SREBP footprint was abolished, but the Sp1 footprint was retained (FIG. 12, lanes 5 and 6).

In gel mobility shift assays, partially purified SREBP produced two shifted bands when incubated with the $^{32}$P-labeled probe that contained two tandem copies of the Repeat 2+3 sequence (FIG. 13A, lanes 5–8). When the amount of SREBP was increased, the amount of the upper band increased progressively, and the amount of the lower band decreased correspondingly. When the probe contained only a single copy of the Repeat 2+3 sequence, only the lower mobility shifted band was observed (lanes 1–4). Moreover, the lower band was the only one visualized when a probe containing all three of the repeats in the native LDL receptor promoter was used, which includes only one copy of Repeat 2 (lanes 9–12). The present inventors concluded that the lower band represents SREBP bound to one copy of Repeat 2 and that the upper band represents binding to two copies.

When a probe that contained one copy of the Repeat 2+3 sequence was used, increasing amounts of purified SREBP produced only one retarded band (FIG. 13B, lanes 1–4) as in FIG. 13A. Purified Sp1 produced a similar band (lane 5, in FIG. 13B). The addition of increasing amounts of purified SREBP in the presence of Sp1 produced increasing amounts of a second band of slower mobility (lanes 6–8), indicating that Sp1 and SREBP were both binding to the oligonucleotide. When the Repeat 3 sequence was mutated to destroy the Sp1 binding site, the probe still bound SREBP (lanes 9–12), but it did not bind Sp1 (lane 13). In the presence of both proteins, the mutant probe produced only the single retarded band that corresponded to the binding of SREBP (lanes 14–16). These data confirm that SREBP can recognize the SRE-1 sequence in Repeat 2, SEQ ID NO:27, in the absence of any contribution from Repeat 3, SEQ ID NO:23, and that the binding of Sp1 and SREBP are additive.

During the course of these studies, SREBP appeared to lose binding activity in the mobility shift assays as the protein became more highly purified. This loss was particularly dramatic after the first two DNA affinity column steps. This loss could be prevented by including a variety of proteins in the assay mixture used for the mobility shift assays. The most effective agent consisted of a preparation of bovine nonfat milk proteins that is frequently used to prevent nonspecific binding on nitrocellulose protein blots. FIG. 14 shows that partially purified SREBP caused no detectable band shift activity when assayed in the absence of milk proteins. Increasing the concentration of milk proteins from 0.3 to 20 µg/tube (0.015 to 1 mg/ml) caused a progressive increase in binding activity. Milk proteins had no binding activity in the absence of SREBP. Comparable concentrations of bovine serum albumin had very little stimulatory effect on SREBP (FIG. 14).

In addition to milk proteins, several other proteins stimulated SREBP activity when tested at 250 µg/ml. These included bovine milk casein, thyroglobulin, fetuin, asialofetuin, bovine submaxillary mucin (type I), fetal calf serum, and the lipoprotein-deficient fraction of newborn calf serum. In addition to bovine serum albumin, other proteins that lacked stimulatory activity included human IgG, bovine milk lactalbumin, and bovine milk lactoglobulin when tested at 250 µg/ml.

C. Discussion

The importance of Repeats 1,2, and 3 in transcription was first demonstrated in 1987 through linker-scanning mutagenesis studies with the LDL receptor promoter (Südhof et al., 1987). Mutations in any of the three 16-bp sequences abolished high-level transcription in the absence of sterols. Repeats 1 and 3 were assigned functions in binding Sp1 based on their conformity with the consensus recognition sequence for this factor and their demonstrated ability to bind Sp1 in vitro (Dawson et al., 1988). Repeat 2 did not conform to this consensus and it did not bind Sp1. When inserted into heterologous promoters, Repeat 3 enhanced transcription constitutively in the absence or presence of sterols, particularly when present in multiple copies (Dawson et al., 1988). Repeat 2 had enhancer activity only when cells were incubated in the absence of sterols and only when it was present together with Repeat 3 or an Sp1 binding site provided by the heterologous promoter (Smith et al., 1990; Dawson et al., 1988). This led to the hypothesis that Repeat 2 contains a conditional enhancer that increases the activity of Repeat 3, but only in sterol-depleted cells (Goldstein and Brown, 1990; Smith et al., 1990). The nature of the putative sterol-regulated protein that recognizes Repeat 2 had not been settled, despite intensive previous efforts (Rajavashisth et al., 1989; Stark et al., 1992).

Studies of point mutants revealed that the active sequence within Repeat 2 is a 10-bp segment designated SRE-1, SEQ ID NO:27 (Smith et al., 1990; Example 1). In the present example, a protein factor has been purified, designated SREBP, that binds specifically to the SRE-1 in a fashion that correlates precisely with the nucleotide-by-nucleotide requirements for sterol-regulated transcription defined in Example 1. Based on this extensive correlation, the present inventors believe that SREBP mediates the conditional enhancer activity of SRE-1.

Identification and purification of SREBP were especially difficult because the factor is present in trace amounts and because nuclear extracts contain several abundant proteins that bind to oligonucleotides containing this sequence, obscuring the binding of SREBP (FIG. 5). These abundant proteins are not involved in regulated transcription because they bind to oligonucleotides that contain point mutations known to inactivate the SRE-1 (Smith et al., 1990; Example 1). After much trial and error, the present inventors found that the pair of mutants designated M and * were the most discriminatory. These contain a T and an A, respectively, in place of the 3'-most C in the SRE-1. The T-containing sequence, which corresponds to the native SRE-1 sequence in the mouse, is active in transcription, whereas the A-containing sequence is inactive (Example 1).

Even with this panel of three discriminatory oligonucleotides, the first steps of purification were carried out in a blind fashion, without being able to assay for specific binding. The empirical purification scheme that was finally employed was based upon lessons learned during the pursuit of several contaminating proteins that bound Repeat 2 in a fashion that did not correlate with physiological function. Now that the SREBP has been identified and purified, it should be possible to refine and streamline the purification scheme, especially after antibodies to SREBP become available.

The final preparation of SREBP, purified more than 38,000-fold, contains a cluster of protein bands between 59 and 68 kDa that bind the SRE-1 in a specific fashion, as indicated by the crosslinking study (FIG. 10). It is possible that all of these bands represent a single protein that is subject to either multiple covalent modifications, such as phosphorylation, or partial proteolysis. It is also possible that SREBP consists of several closely related proteins. These questions will be resolved only when larger amounts of SREBP are available and when protein sequence data have been obtained.

When subjected to size fractionation by gel filtration early in the purification, SREBP emerged from the column at a position corresponding to a molecular mass of 500 kDa (FIG. 6). In contrast, the purified protein sedimented on glycerol gradient centrifugation at a slower rate than ovalbumin ($M_r$ 44,000) (FIG. 9). These observations may indicate that SREBP exists as a multiprotein complex which dissociates during purification, or that SREBP is an elongated molecule which behaves anomalously on gel filtration.

In the gel mobility shift assays, the activity of purified SREBP was stimulated markedly by a variety of proteins, including the components of nonfat bovine milk. This enhancing activity was originally noted in the flow-through fraction from the first Repeat 2-containing DNA affinity column. The stimulatory effect was not entirely nonspecific since proteins such as albumin and immunoglobulins failed to substitute. It is possible that a further protein may enhance SREBP activity, but SREBP is clearly active under the conditions described herein.

The availability of the SREBP protein will allow, for the first time, the means by which cells regulate SREBP activity in response to cholesterol to be investigated. Having the purified protein will also allow the generation of poly- and monoclonal antibodies against this protein and will enable the molecular cloning of cDNAs and/or genes encoding the SREBP protein to be achieved. By means of the protein itself and the other biological products which can now be obtained, the inventors propose to determine how the addition of sterols prevents SREBP-mediated transcription of the LDL receptor gene. For example, sterols may prevent the entry of SREBP into the nucleus, decrease its ability to bind to SRE-1, decrease the ability of the bound protein to activate transcription or may act via a combination of these or other mechanisms. Now that SREBP protein is available, these potential mechanisms can be probed at the molecular level.

In addition to the LDL receptor gene, the genes for 3-hydroxy-3-methylglutaryl CoA (HMG CoA) synthase and HMG CoA reductase are repressed by sterols (Goldstein and Brown, 1990). The 5' flanking region of the HMG CoA synthase gene contains three regions that are required for sterol-regulated transcription (Smith et al., 1988). Two of these regions contain SRE-1 sequences that may conform to the requirements for binding of SREBP. The 5' flanking region of the HMG CoA reductase gene also contains a region that is necessary for sterol-mediated regulation (Goldstein and Brown, 1990; Osborne et al., 1988). This region contains a sequence that loosely resembles the SRE-1, which led to the suggestion that the HMG CoA reductase gene might be regulated by the same protein that regulates the LDL receptor (Smith et al., 1988). More extensive mutagenesis studies (Osborne, 1991) indicate that the putative sterol regulatory element in HMG CoA reductase should not bind to SREBP as defined in the current studies (Example 1). Moreover, Osborne et al. (1992) have recently identified a protein designated Red25 that recognizes the sterol-sensitive HMG CoA reductase sequence. This protein does not recognize the SRE-1 from the LDL receptor, indicating that the control mechanisms for the two genes are distinct.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter can be made without undue experimentation.

REFERENCES

The following references, to the extent that they provide exemplary procedural or other details supplementary to those set forth herein, are specifically incorporated herein by reference.

Ayer et al.. (1993) *Cell,* 72: 211–222.

Bishop, R. W. (1992) *J. Lipid Res.* 33, 549–557.

Briggs, M. R., Kadonaga, J. T., Bell, S. P., and Tjian, R. (1986) *Science* 234, 47–52.

Brown, M. S. and Goldstein, J. L. (1986) *Science* 232, 34–47.

Chodosh, L. A., Carthew, R. W., and Sharp, P. A. (1986) *Mol. Cell. Biol.* 6, 4723–4733.

Dawson, P. A., Hofmann, S. L., van der Westhuyzen, D. R., Brown, M. S., and Goldstein, J. L. (1988) *J. Biol. Chem.* 263, 3372–3379.

Dignam, J. D., Lebovitz, R. M., and Roeder, R. G. (1983) *Nucl. Acids Res.* 11, 1475–1489.

Freedman, L. P., Yoshinaga, S. K., Vanderbilt, J. N., and Yamamoto, K. R. (1989) *Science* 245, 298–301.

Gil, G., Smith, J. R., Goldstein, J. L., Slaughter, C. A., Orth K., Brown, M. S. and Osborne, T. F. (1988) *Proc. Natl. Acad. Sci. USA* 85, 8963–8967.

Gil, G., Osborne, T. F., Goldstein, J. L. and Brown, M. S. (1988) *J. Biol. Chem.* 263, 19009–19019.

Goldstein, J. L., Basu, S. K., and Brown, M. S. (1983) *Meth. Enzymol.* 98, 241–260.

Goldstein, J. L. and Brown, M. S. (1990) *Nature* 343, 425–430.

Goodbourn et al. (1986), *Cell,* 45: 601–610.

Gorman, C. M., Moffat, L. F., and Howard, B. H. (1982) *Mol. Cell. Biol.* 2, 1044–1051.

Jacob et al. (1961), *J. Mol. Biol.,* 3: 318–350.

Kadonaga, J. T. and Tjian, R. (1986) *Proc. Natl. Acad. Sci. USA* 83, 5889–5893.

Klein-Hitpass, L., Tsai, S. Y., Weigel, N. L., Allan, G. F., Riley, D., Rodriguez, R., Schrader, W. T., Tsai, M. J., and O'Malley, B. W. (1990) *Cell* 60, 247–257.

Laemmli, U. K. (1970) *Nature* 227, 680–685.

Lee, F., Hall, C. V., Ringold, G. M., Dodson, D. E., Luh, J., and Jacob, P. E. (1984) *Nucl. Acid. Res.* 12, 4191–4206.

Lichtsteiner, S., Wuarin, J., and Schibler, U. (1987) *Cell* 51, 963–973.

Lillie, J. W. and Green, M. R. (1989) *Nature* 338, 39–44.

Lowry, O. H., Rosebrough, N. J., Farr, A. L., and Randall, R. J. (1951) *J. Biol. Chem.* 193, 265–275.

Mehta, K. D., Brown, M. S., Bilheimer, D. W., and Goldstein, J. L. (1991) *J. Biol. Chem.* 266, 10415–10419.

Osborne et al., *Cell,* 42: 203–212 (1985).

Osborne, T. F., Gil, G., Goldstein, J. L. & Brown, M. S. (1988) *J. Biol. Chem.* 263, 3380–3387.

Osborne, T. F. (1991) *J. Biol. Chem.* 266, 13947–13951.

Osborne, T. F., Bennett, M. & Rhee, K. (1992) *J. Biol. Chem.* 267, 18973–18982.

Pascal, E. and Tjian, R. (1991) *Genes & Dev.* 5, 1646–1656.

Pothier, F., Ouellet, M., Julien, J. P., and Guerin, S. L. (1992) *DNA Cell Biol.* 11, 83–90.

Rajavashisth, T. B., Taylor, A. K., Andalibi, A., Svenson, K. L., and Lusis, A. J. (1989) *Science* 245, 640–643.

Sambrook, J., Fritsch, E. F., and Maniatis, T. (1989) *Molecular cloning: A laboratory manual,* Cold Spring Harbor Laboratory Press, New York.

Seed, B. and Sheen, J. Y. (1988) *Gene* 67, 271–277.

Smith, J. R., Osborne, T. F., Brown, M. S., Goldstein, J. L., and Gil, G. (1988) *J. Biol. Chem.* 263, 18480–18487.

Smith, J. R., Osborne, T. F., Goldstein, J. L., and Brown, M. S. (1990) *J. Biol. Chem.* 265, 2306–2310.

Stark, H. C., Weinberger, O., and Weinberger, J. (1992) *Proc. Natl. Acad. Sci. USA* 89, 2180–2184.

Stuart et al. (1984), *Proc. Natl. Acad. Sci. USA,* 81: 7318–7322.

Sudhof, T. C., van der Westhuyzen, D. R., Goldstein, J. L., Brown, M. S., and Russell, D. W. (1987) *J. Biol. Chem.* 262, 10773–10779.

Yamamoto (1985), *Ann. Rev. Genet.,* 19: 209–252.

---

What is claimed is:

1. An isolated protein which exhibits a molecular weight of between about 59 kD and about 68 kD in sodium dodecyl sulfate polyacrylamide gels and binds with sequence specificity to the sterol regulatory element SRE-1 (SEQ ID NO:27).

2. The protein of claim 1, purified to between about 200-fold and about 38,000-fold relative to its natural state.

3. The protein of claim 2, purified to about 38,000-fold relative to its natural state.

4. The protein of claim 1 purified to homogeneity.

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AAAATCACCC CACTGCAA                                        18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TAAATCACCC CACTGCAA                                        18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATAATCACCC CACTGCAA                                        18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:4:

AATATCACCC CACTGCAA 18

(2) INFORMATION FOR SEQ ID NO:5:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

AAATTCACCC CACTGCAA 18

(2) INFORMATION FOR SEQ ID NO:6:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

AAAAGCACCC CACTGCAA 18

(2) INFORMATION FOR SEQ ID NO:7:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

AAAATAACCC CACTGCAA 18

(2) INFORMATION FOR SEQ ID NO:8:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

AAAATCTCCC CACTGCAA 18

(2) INFORMATION FOR SEQ ID NO:9:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

AAAATCAACC CACTGCAA 18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AAAATCACGC CACTGCAA 18

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

AAAATCACCG CACTGCAA 18

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AAAATCACCC AACTGCAA 18

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AAAATCACCC CTCTGCAA 18

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

AAAATCACCC CAATGCAA 18

( 2 ) INFORMATION FOR SEQ ID NO:15:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

AAAATCACCC CACGGCAA　　　　　　　　　　　　　　　　　　　　　　　　　　　　18

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

AAAATCACCC CACTTCAA　　　　　　　　　　　　　　　　　　　　　　　　　　　　18

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

AAAATCACCC CACTGAAA　　　　　　　　　　　　　　　　　　　　　　　　　　　　18

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AAAATCACCC CACTGCTA　　　　　　　　　　　　　　　　　　　　　　　　　　　　18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

AAAATCACCC CACTGCAT　　　　　　　　　　　　　　　　　　　　　　　　　　　　18

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:20:

AAAATCACAC CACTGCAA                   18

( 2 ) INFORMATION FOR SEQ ID NO:21:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

AAAATCACCC CATTGCAA                   18

( 2 ) INFORMATION FOR SEQ ID NO:22:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

AAAATCACCC CACTGC                     16

( 2 ) INFORMATION FOR SEQ ID NO:23:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

AAACTCCTCC CCCTGC                     16

( 2 ) INFORMATION FOR SEQ ID NO:24:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

AAAATCACCC CACTGCAAAC TCCTCCCCCT GC    32

( 2 ) INFORMATION FOR SEQ ID NO:25:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

AAAAGAACCC CTATGCAAAC TCCTCCCCCT GC    32

( 2 ) INFORMATION FOR SEQ ID NO:26:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TGAAGCTTGC ATGCCTGCAG GTCGACTCGA CTCTAGAGGG TATATAATGG ATCCCCGGGT    60

ACCGAGCTCG AATTCATCAG CTTGGCGAGA TTTTCAGGAG CTAAGGAAGC TAAAATG    117

( 2 ) INFORMATION FOR SEQ ID NO:27:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

ATCACCCCAC    10

( 2 ) INFORMATION FOR SEQ ID NO:28:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GACACTATAG AACTCGAGCA GCTGAAGCTT GCATGC    36

( 2 ) INFORMATION FOR SEQ ID NO:29:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GGTACCCGGG GATCCATTAT ATACC    25

( 2 ) INFORMATION FOR SEQ ID NO:30:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

TCGACAAAAG ATAAGATGTG CAAACTCCTC CCCCTGCG    38

( 2 ) INFORMATION FOR SEQ ID NO:31:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

TCGACAAAAG ATAAGATATG CAAACTCCTC CCCCTGCG    38

( 2 ) INFORMATION FOR SEQ ID NO:32:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

TCGACGCAGG GGGAGGAGTT TGCATATCTT ATCTTTTG    38

( 2 ) INFORMATION FOR SEQ ID NO:33:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

TCGACAAAAT CACCCCACTG TAAAATCACC CCACTGTG    38

( 2 ) INFORMATION FOR SEQ ID NO:34:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

TCGACACAGT GGGGTGATTT TACAGTGGGG TGATTTTG    38

( 2 ) INFORMATION FOR SEQ ID NO:35:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

GATCATCACC CCACTG    16

( 2 ) INFORMATION FOR SEQ ID NO:36:

( i ) SEQUENCE CHARACTERISTICS:
        ( A ) LENGTH: 16 base pairs

-continued (B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:36:

GATCCAGTGG GGTGAT    16